United States Patent
O'Connor et al.

(10) Patent No.: US 6,277,871 B1
(45) Date of Patent: Aug. 21, 2001

(54) INHIBITORS OF PROTEIN ISOPRENYL TRANSFERASES

(75) Inventors: Stephen J. O'Connor, Guilford, CT (US); Lissa T. J. Nelson, Highland Park, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/442,687

(22) Filed: Nov. 18, 1999

Related U.S. Application Data

(60) Provisional application No. 60/109,347, filed on Nov. 20, 1998.

(51) Int. Cl.[7] ............ A61K 31/4418; C07D 211/94
(52) U.S. Cl. ................................. 514/354; 546/323
(58) Field of Search ............... 546/323; 514/354

(56) References Cited

U.S. PATENT DOCUMENTS 5,965,539 * 10/1999 Sebti et al. ................ 514/19

FOREIGN PATENT DOCUMENTS 9500497  1/1995 (WO).
9717070  5/1997 (WO).

* cited by examiner

Primary Examiner—Alan L. Rotman
Assistant Examiner—Rita Desai
(74) Attorney, Agent, or Firm—B. Gregory Donner; Gregory W. Steele

(57) ABSTRACT

The present invention relates to novel compounds of Formula I

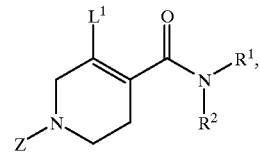

which are useful in inhibiting protein isoprenyl transferases and the farnesylation or geranylgeranylation of the oncogene protein Ras and other related small g-proteins, and compositions containing such compounds and methods of using such compounds.

7 Claims, No Drawings

INHIBITORS OF PROTEIN ISOPRENYL TRANSFERASES

This application claims the benefit of U.S. Provisional Application for Patent No. 60/109,347, filed Nov. 20, 1998.

The present invention relates to novel compounds which are useful in inhibiting protein isoprenyl transferases (for example, protein farnesyltransferase and protein geranylgeranyltransferase) and the farnesylation or geranylgeranylation of the oncogene protein Ras and other related small g-proteins, compositions containing such compounds and methods of using such compounds.

BACKGROUND OF THE INVENTION

Ras oncogenes are the most frequently identified activated oncogenes in human tumors. Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase, and thereby farnesylation of the Ras protein, blocks the ability of transformed cells to proliferate. Inhibition of protein geranylgeranyltransferase and, thereby, of geranylgeranylation of Ras proteins, also results in down regulation of Ras protein function.

Activation of Ras and other related small g-proteins that are farnesylated and/or geranylated also partially mediates smooth muscle cell proliferation (Circulation, I-3: 88 (1993), which is hereby incorporated herein by reference). Inhibition of protein isoprenyl transferases, and thereby farnesylation or geranylgeranylation of the Ras protein, also aids in the prevention of intimal hyperplasia associated with restenosis and atherosclerosis, a condition which compromises the success of angioplasty and surgical bypass for obstructive vascular lesions.

There is therefore a need for compounds which are inhibitors of protein farnesyltransferase and protein geranylgeranyltransferase.

SUMMARY OF THE INVENTION

In its principle embodiment, the present invention provides a compound of Formula I

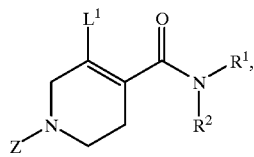

I or a pharmaceutically acceptable salt or prodrug thereof, where
$L^1$ is selected from
(1) phenyl,
(2) naphthyl,
(3) dihydronaphthyl,
(4) tetrahydronaphthyl,
(5) indanyl,
(6) indenyl, and
(7) cycloalkyl
where (1)–(7) can be optionally substituted with 1 or 2 substituents independently selected from
(a) alkyl,
(b) halogen,
(c) perfluoroalkyl, and
(d) —$OR^3$ where $R^3$ is selected from
(a) hydrogen and
(b) alkyl;
$R^1$ and $R^2$ are independently selected from
(1) hydrogen and
(2) alkyl where alkyl can be optionally substituted with 1, 2, or 3 substituents independently selected from
(a) —$CO_2R^4$ where $R^4$ is selected from
(i) hydrogen,
(ii) alkyl, and
(iii) a carboxy-protecting group,
(b) —$C(O)NR^5R^6$ where $R^5$ and $R^6$ are independently selected from
(i) hydrogen,
(ii) alkyl,
(iii) an amino-protecting group, and
(iv) —$S(O)_tR^7$ where $R^7$ is selected from
hydrogen,
alkyl, and
aryl, and
t is an integer from 0 to 2,
(c) —$S(O)_tR^7$,
(d) aryl,
(e) heterocycle,
(f) —$OR^8$ where $R^8$ is selected from
(i) hydrogen,
(ii) cycloalkyl,
(iii) a hydroxy-protecting group, and
(iv) alkyl where alkyl can be optionally substituted with 1 or 2 substituents independently selected from
cycloalkyl,
aryl, and
heterocycle,
(g) —$SO_3H$,
(h) —$NR^5R^6$,
(i) —$NR^9C(O)NR^{10}R^{11}$ where $R^9$, $R^{10}$, and $R^{11}$ are independently selected from
(i) hydrogen,
(ii) alkyl, and
(iii) —OH,
(j) —$NHC(O)NHNH_2$,
(k) —$NHC(NH)NH_2$, and
(l) cycloalkyl;
Z is selected from
(1) —$C(O)R^{12}$ where $R^{12}$ is selected from
(a) —$NR^{13}R^{14}$ where $R^{13}$ and $R^{14}$ are independently selected from
(i) hydrogen,
(ii) aryl,
(iii) heterocycle,
(iv) an amino-protecting group,
(v) cycloalkyl, and
(vi) alkyl where alkyl can be optionally substituted with 1, 2, or 3 substituents independently selected from
—$CO_2R^4$,
—$C(O)NR^5R^6$,
—$NR^5R^6$,
—$S(O)_tR^7$,
—$OR^{15}$ where $R^{15}$ is selected from
hydrogen,
cycloalkyl,
alkyl where alkyl can be optionally substituted with 1, 2, or 3 substituents independently selected from —CO$_2$R$^4$,
—C(O)NR$^5$R$^6$,
—NR$^5$R$^6$,
—S(O)$_r$R$^7$,
cycloalkyl,
aryl, and
heterocycle,
aryl,
heterocycle, and
a hydroxy-protecting group,
cycloalkyl,
aryl, and
heterocycle,
(b) alkyl where alkyl can be optionally substituted with 1, 2, or 3 substituents independently selected from
(i) —CO$_2$R$^4$,
(ii) —C(O)NR$^{13}$R$^{14}$,
(iii) —NR$^{13}$R$^{14}$,
(iv) —OR$^{16}$ where R$^{16}$ is selected from
hydrogen,
cycloalkyl,
alkyl where alkyl can be optionally substituted with 1, 2, or 3 substituents independently selected from
—CO$_2$R$^4$,
—C(O)NR$^{13}$R$^{14}$,
—NR$^{13}$R$^{14}$,
—OR$^8$,
—S(O)$_r$R$^7$,
cycloalkyl,
aryl, and
heterocycle,
aryl,
heterocycle, and
a hydroxy-protecting group,
(v) —S(O)$_r$R$^7$,
(vi) cycloalkyl,
(vii) aryl, and
(viii) heterocycle,
(c) —OR$^{16}$, and
(d) alkenyl where alkenyl can be optionally substituted with 1 or 2 substituents independently selected from
(i) —CO$_2$R$^4$,
(ii) —C(O)NR$^{13}$R$^{14}$,
(iii) —NR$^{13}$R$^{14}$,
(iv) —OR$^{16}$,
(v) —S(O)$_r$R$^7$,
(vi) cycloalkyl,
(vii) aryl, and
(viii) heterocycle,
(2) alkyl where alkyl can be optionally substituted with 1, 2, or 3 substituents independently selected from
(a) —CO$_2$R$^4$,
(b) —C(O)NR$^{13}$R$^{14}$,
(c) —C(O)R$^{12}$,
(d) —NR$^{13}$R$^{14}$,
(e) —NR$^{13}$C(O)R$^{12}$,
(f) —OC(O)R$^{12}$,
(g) —OR$^{16}$,
(h) —SO$_2$NR$^{13}$R$^{14}$,
(i) cycloalkyl,
(j) aryl, and
(k) heterocycle, and
(3) —SO$_2$NR$^{13}$R$^{14}$;
where at each occurrence in R$^1$, R$^2$, and Z aryl can be optionally substituted with 1, 2, or 3 substituents independently selected from (1) alkenyl where alkenyl can be optionally substituted with 1 or 2 substituents independently selected from
(a) —CO$_2$R$^4$,
(b) —C(O)NR$^{13}$R$^{14}$,
(c) —C(O)R$^{12}$,
(d) —NR$^{13}$R$^{14}$,
(e) —NR$^{13}$C(O)R$^{12}$,
(f) —OC(O)R$^{12}$,
(g) —OR$^{16}$,
(h) —SO$_2$NR$^{13}$R$^{14}$,
(i) cycloalkyl,
(j) aryl, and
(k) heterocycle,
(2) alkyl where alkyl can be optionally substituted with 1, 2, or 3 substituents independently selected from
(a) —CO$_2$R$^4$,
(b) —C(O)NR$^{13}$R$^{14}$,
(c) —C(O)R$^{12}$,
(d) —NR$^{13}$R$^{14}$,
(e) —NR$^{13}$C(O)R$^{12}$,
(f) —OC(O)R$^{12}$,
(g) —OR$^{16}$,
(h) —SO$_2$NR$^{13}$R$^{14}$,
(i) cycloalkyl,
(j) aryl, and
(k) heterocycle,
(3) alkynyl where alkynyl can be optionally substituted with 1 or 2 substituents independently selected from
(a) —CO$_2$R$^4$,
(b) —C(O)NR$^{13}$R$^{14}$,
(c) —C(O)R$^{12}$,
(d) —NR$^{13}$R$^{14}$,
(e) —NR$^{13}$C(O)R$^{12}$,
(f) —OC(O)R$^{12}$,
(g) —OR$^{16}$,
(h) —SO$_2$NR$^{13}$R$^{14}$,
(i) cycloalkyl,
(j) aryl, and
(k) heterocycle,
(4) aryl where aryl can be optionally substituted with 1, 2, or 3 substituents independently selected from
(a) alkenyl,
(b) alkyl,
(c) alkynyl,
(d) —CO$_2$R$^4$,
(e) —CN,
(f) halogen,
(g) haloalkyl,
(h) —NO$_2$,
(i) —NR$^5$R$^6$,
(j) —OR$^8$,
(k) perfluoroalkyl,
(l) oxo (=O), and
(m) —S(O)$_r$R$^7$,
(5) heterocycle where heterocycle can be optionally substituted with 1, 2, or 3 substituents independently selected from
(a) alkenyl,
(b) alkyl,
(c) alkynyl,
(d) —CO$_2$R$^4$,
(e) —CN,
(i) halogen,
(g) haloalkyl,
(h) —NO$_2$,
(i) —NR$^{13}$R$^{14}$,
(j) —OR$^{16}$, (k) perfluoroalkyl,
(l) oxo (=O), and
(m) —S(O)$_r$R$^7$,
(6) —CO$_2$R$^4$,
(7) —CN,
(8) halogen,
(9) haloalkyl,
(10) —NO$_2$,
(11) —NR$^{13}$R$^{14}$,
(12) —OR$^{16}$,
(13) perfluoroalkyl,
(14) oxo (=O), and
(15) —S(O)$_r$R$^7$;
where at each occurrence in R$^1$, R$^2$, and Z heterocycle can be optionally substituted with 1 or 2 substituents independently selected from
(1) alkenyl where alkenyl can be optionally substituted with 1 or 2 substituents independently selected from
  (a) —CO$_2$R$^4$,
  (b) —C(O)NR$^{13}$R$^{14}$,
  (c) —C(O)R$^{12}$,
  (d) —NR$^{13}$R$^{14}$,
  (e) —NR$^{13}$C(O)R$^{12}$,
  (f) —OC(O)R$^{12}$,
  (g) —OR$^{16}$,
  (h) —SO$_2$NR$^{13}$R$^{14}$,
  (i) cycloalkyl,
  (j) aryl, and
  (k) heterocycle,
(2) alkyl where alkyl can be optionally substituted with 1, 2, or 3 substituents independently selected from
  (a) —CO$_2$R$^4$,
  (b) —C(O)NR$^{13}$R$^{14}$,
  (c) —C(O)R$^{12}$,
  (d) —NR$^{13}$R$^{14}$,
  (e) —NR$^{13}$C(O)R$^{12}$.
  (f) —OC(O)R$^{12}$,
  (g) —OR$^{16}$,
  (h) —SO$_2$NR$^{13}$R$^{14}$,
  (i) cycloalkyl,
  (j) aryl, and
  (k) heterocycle,
(3) alkynyl where alkynyl can be optionally substituted with 1 or 2 substituents independently selected from
  (a) —CO$_2$R$^4$,
  (b) —C(O)NR$^{13}$R$^{14}$,
  (c) —C(O)R$^{12}$,
  (d) —NR$^{13}$R$^{14}$,
  (e) —NR$^{13}$C(O)R$^{12}$,
  (f) —OC(O)R$^{12}$,
  (g) —OR$^{16}$,
  (h) —SO$_2$NR$^{13}$R$^{14}$,
  (i) cycloalkyl,
  (j) aryl, and
  (k) heterocycle,
(4) aryl where aryl can be optionally substituted with 1, 2, or 3 substituents independently selected from
  (a) alkenyl,
  (b) alkyl,
  (c) alkynyl,
  (d) —CO$_2$R$^4$,
  (e) —CN,
  (f) halogen,
  (g) haloalkyl,
  (h) —NO$_2$,
  (i) —NR$^{13}$R$^{14}$,
  (j) —OR$^{16}$,
  (k) perfluoroalkyl,
  (l) oxo (=O), and
  (m) —S(O)$_r$R$^7$,
(5) heterocycle where heterocycle can be optionally substituted with 1, 2, or 3 substituents independently selected from
  (a) alkenyl,
  (b) alkyl,
  (c) alkynyl,
  (d) —CO$_2$R$^4$,
  (e) —CN,
  (f) halogen,
  (g) haloalkyl,
  (h) NO$_2$,
  (i) —NR$^{13}$R$^{14}$,
  (j) —OR$^{16}$,
  (k) perfluoroalkyl,
  (l) oxo (=O), and
  (m) —S(O)$_r$R$^7$,
(6) —CO$_2$R$^4$,
(7) —CN,
(8) halogen,
(9) haloalkyl
(10) —NO$_2$,
(11) —NR$^{13}$R$^{14}$,
(12) —OR$^{16}$,
(13) perfluoroalkyl,
(14) oxo (=O), and
(15) —S(O)$_r$R$^7$.

In a further aspect of the present invention are disclosed pharmaceutical compositions which comprise a compound of Formula I in combination with a pharmaceutically acceptable carrier alone or in combination with another chemotherapeutic agent.

In yet another aspect of the present invention are disclosed pharmaceutical compositions for the treatment of cancer comprising a compound of Formula I in combination with a pharmaceutically acceptable carrier alone or in combination with another chemotherapeutic agent.

In yet another aspect of the present invention are disclosed pharmaceutical compositions for inhibiting post-translational modification of the oncogenic Ras protein by protein farnesyltransferase, protein geranylgeranyltransferase, or both comprising a compound of Formula I in combination with a pharmaceutically acceptable carrier.

In yet another aspect of the present invention are disclosed pharmaceutical compositions for treating or preventing restenosis in a mammal comprising a compound of Formula I in combination with a pharmaceutically acceptable carrier.

In yet another aspect of the present invention is disclosed a method for inhibiting protein isoprenyl transferases (i.e., protein farnesyltransferase and/or geranylgeranyltransferase) in a human or lower mammal, comprising administering to the patient a therapeutically effective amount of a compound of Formula I.

In yet another aspect of the present invention is disclosed a method for inhibiting post-translational modification of the oncogenic Ras protein by protein farnesyltransferase, protein geranylgeranyltransferase or both.

In yet another aspect of the present invention is disclosed a method for treatment of conditions mediated by farnesylated or geranylgeranylated proteins, for example, treatment of Ras associated tumors in humans and other mammals.

In yet another aspect of the present invention is disclosed a method for inhibiting or treating cancer in a human or lower mammal comprising administering to the patient a therapeutically effective amount of a compound of Formula I alone or in combination with another chemotherapeutic agent In yet another aspect of the present invention is disclosed a method for treating or preventing intimal hyperplasia associated with restenosis and atherosclerosis in a mammal comprising administering to the mammal a therapeutically effective amount of a compound of Formula I.

In yet another embodiment of the present invention is disclosed pharmaceutical compositions containing compounds of Formula I.

Compounds of this invention include, but are not limited to,

N-4-[1-(3-Cyclohexylpropyloxycarbonyl)-3-(2-methylphenyl)-1,2,5,6-tetrahydroisonicotinyl] methionine, N-4-[1-(3-[5-Thiazolyl]acryloyl)-3-(2-methylphenyl)-1,2,5,6-tetrahydroisonicotinyl]methionine, N-4-[1-(N'-Benzyl-5-thiazolmethylaminocarbonyl)-3-(2-methylphenyl)-1,2,5,6-tetrahydroisonicotinyl] methionine, N-[N'-(3-Phenylpropyl)-3-(2-methylphenyl)-1,2,5,6-tetrahydroisonicotinyl]methionine, N-[N'-(3-Pyridylacetyl)-3-(2-methylphenyl)-1,2,5,6-tetrahydroisonicotinyl]methionine, N-4-[1-(N'-Benzyl-5-thiazolmethylaminosulfamoyl)-3-(2-methylphenyl)-1,2,5,6-tetrahydroisonicotinyl] methionine, N-4-[1-N'-(2-Benzyl-2-(4-thiazolylmethyl)glycinoyl)-3-(2-methylphenyl)-1,2,5,6-tetrahydroisonicotinyl] methionine, N-4-[1-N'-(2-Benzyl-2-(4-thiazolylmethyl)aminoacetyl)-3-(2-methylphenyl)-1,2,5,6-tetrahydroisonicotinyl] methionine, N-4-[1-N'-(2-Benzyl-2-(2-thiazolylmethyl)aminoacetyl)-3-(2-methylphenyl)-1,2,5,6-tetrahydroisonicotinyl] methionine, N-4-[1-(2-[N"-Benzyl-N"-2-thiazolylmethyl)acetamido)-3-(2-methylphenyl)-1,2,5,6-tetrahydroisonicotinyl] methionine, methyl ester, N-[4-[(5-(4-Chlorophenyl)-2-methoxycarbonylfuranyl)-3-(2-methylphenyl)-1,2,5,6-tetrahydroisonicotinyl] methionine, N-4-[1-N'-(N"-2-Cyclhexylethylmethylglycinoyl)-3-(2-methylphenyl)-1,2,5,6-tetrahydroisonicotinyl] methionine, N-4-[1-N'-(N"-2-Cyclhexylethylmethylaminocarbonyl)-3-(2-methylphenyl)-1,2,5,6-tetrahydroisonicotinyl] methionine, N-4-[(N'-2-Benzyloxyacetyl)-3-(2-methylphenyl)-1,2,5,6-tetrahydroisonicotinyl]methionine, N-4-[(N'-2(S)-1-Ethylthio-3-cyclohexyl-2-propoxycarbonyl)-3-(2-methylphenyl)-1,2,5,6-tetrahydroisonicotinyl]methionine, lithium salt, N-4-[(N'-2-Cyclohexyloxyethoxycarbonyl)-3-(2-methylphenyl)-1,2,5,6-tetrahydroisonicotinyl] methionine, lithium salt, N-4-[1-N'-(N"-2-Cyclhexylethylmethylaminocarbonyl)-3-(2-methylphenyl)-1,2,5,6-tetrahydroisonicotinyl] methionine, N-4-[1-(4-Phenoxybutyl)-3-(2-methylphenyl)-1,2,5,6-tetrahydroisonicotinyl]methionine, N-4-[1-(2-[R*,S*]-Benzyloxyhexyl)-3-(2-methylphenyl)-1,2,5,6-tetrahydroisonicotinyl] methionine, lithium salt, N-4-[1-(2-[R*,S*]-Cyclohexylmethyloxyhexyl)-3-(2-methylphenyl)-1,2,5,6-tetrahydroisonicotinyl] methionine, lithium salt, N-4-[1-(2-[R*,S *]-5-(1-Hydroxy-3-cyclohexylpropyl) thiazolyloxycarbonyl)-3-(2-methylphenyl)-1,2,5,6-tetrahydroisonicotinyl]methionine, lithium salt, N-4-[1-(4-Methyl-[R*,S*]-5-(1-hydroxy-2-cyclohexylethyl)thiazolyloxycarbonyl)-3-(2-methylphenyl)-1,2,5,6-tetrahydroisonicotinyl] methionine, methyl ester, N-[4-(2',2'-bisCyclohexylmethyl-2'-aminoethyl)-3-(2-methylphenyl)-1,2,5,6-tetrahydroisonicotinyl] methionine, lithium salt, N-[4-(2',2'-bis(5-Thiazolemethyl)-2'-aminoethyl)-3-(2-methylphenyl)-1,2,5,6-tetrahydroisonicotinyl] methionine, lithium salt, N-[4-(2',2'-di-Butyl-2'-aminoethyl)-3-(2-methylphenyl)-1,2,5,6-tetrahydroisonicotinyl]methionine, lithium salt, N-[4-(2',2'-di-Butyl-2'-aminoethyl)-3-(2-methylphenyl)-1,2,5,6-tetrahydroisonicotinyl]methionine, N-[4-((N'-(2-Cyclohexyloxyethyl)-N'-butyl)-2'-aminoethyl)-3-(2-methylphenyl)-1,2,5,6-tetrahydroisonicotinyl]methionine, lithium salt, and N-[4-(2(S)-(Cyclohexyloxymethylpyrrolidinyl)ethyl)-3-(2-methylphenyl)-1,2,5,6-tetrahydroisonicotinyl] methionine, lithium salt.

DETAILED DESCRIPTION OF THE INVENTION

Definition of Terms

The term "alkenyl" refers to a straight or branched chain hydrocarbon radical containing from 2-to-10 carbon atoms formed by the removal of a single hydrogen atom and also containing at least one carbon-carbon double bond formed by the removal of two hydrogen atoms. Representative examples of "alkenyl" include but are not limited vinyl, 2-propenyl, 2-methyl-2-propenyl, 3-butenyl, 4-pentenyl, 5-hexcnyl, cis-2-heptene, trans-2-heptene, 2-methyl-1-heptene, trans-3-decene and the like.

The term "alkyl" refers to a straight or branched chain hydrocarbon radical containing from 1-to-10 carbon atoms formed by the removal of a single hydrogen atom. Representative examples of "alkyl" include but are not limited to methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. The alkyl groups can be optionally interrupted by one or more heteroatoms selected from the group consisting of oxygen, nitrogen, and sulfur.

The term "alkynyl" refers to a straight or branched chain hydrocarbon radical containing from 2-to-10 carbon atoms formed by the removal of a single hydrogen atom and also containing at least one carbon-carbon triple bond formed by the removal of four hydrogen atoms. Representative examples of "alkynyl" include but are not limited to acetylenyl, 1-propynyl, 2-propynyl, 3-butynyl, 2-pentynyl, 1-butynyl and the like.

The term "amino" refers to —NH$_2$.

The term "amino-protecting group" refers to groups intended to protect an amino group against undersirable reactions during synthetic procedures. Commonly used N-protecting groups are disclosed in Greene, T. W., & Wuts, P. G. M. (1991). *Protectective Groups In Organic Synthesis* (2nd ed.). New York: John Wiley & Sons. Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "aryl" refers to a carbocyclic ring system having 6-to-10 ring atoms and one or two aromatic rings. Representative examples of "aryl" groups include but are not limited to phenyl, naphthyl, tetrahydronaphthyl, indanyl, indenyl and the like.

The term "a carboxy-protecting group" refers to a carboxylic acid protecting ester or amide group typically employed to block or protect the carboxylic acid functionality while the reactions involving other functional sites of the compound are performed. Carboxy protecting groups are disclosed in Greene, T. W., & Wuts, P. G. M. (1991). *Protectective Groups In Organic Synthesis* (2nd ed.). New York: John Wiley & Sons. Additionally, a carboxy-protecting group can be used as a prodrug whereby the carboxy-protecting group can be readily cleaved in vivo, for example by enzymatic hydrolysis, to release the biologically active parent. Such carboxy-protecting groups are well known to those skilled in the art, U.S. Pat. No. 3,840,556 and 3,719,667.

The term "cycloalkyl" refers to a saturated cyclic hydrocarbon radical containing from 3-to-8 carbon atoms formed by the removal of a single hydrogen atom. Representative examples of "cycloalkyl" include cyclopropyl, cyclobutyl, cyclopentyl, cyclohexyl, cycloheptyl, cyclooctyl and the like.

The terms "Cys," "Glu," "Ile," "Leu," "Lys," "Met," "nor-Leu," "nor-Val," "Phe," "Ser," "Thr," and "Val" refer to cysteine, glutamine, isoleucine, leucine, lysine, methionine, norleucine, norvaline, phenylalanine, serine, threonine and valine respectively in their L-, D- or DL forms.

The term "halo" or "halogen" refers to F, Cl, Br, or I.

The term "haloalkyl" refers to a straight or branched chain hydrocarbon radical containing from 1-to-6 carbon atoms formed by the removal of a single hydrogen atom in which one or more hydrogen atoms has been replaced with a halogen. Representative examples of "haloalkyl" include but are not limited to trifluoromethyl, trichloromethyl, difuoromethyl, dichloromethyl, fluoromethyl, chloromethyl, chloroethyl, 2,2,2-trifluoroethyl, 2,2-dichloroethyl and the like.

The term "heterocycle" represents a represents a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups where a monocyclic heterocyclic group is bridged by an alkylene group such as

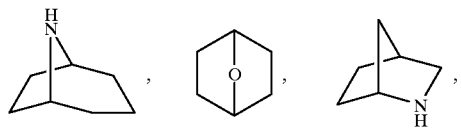

and the like.

Heterocyclics also include compounds of the formula

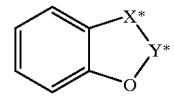

where X* is selected from —CH$_2$—, —CH$_2$O— and —O—, and Y* is selected from —C(O)— and —(C(R"")$_2$)$_v$—, where R" is hydrogen or alkyl of one to four carbons, and v is 1–3. These heterocycles include 1,3-benzodioxolyl, 1,4-benzodioxanyl, and the like.

The term "hydroxy-protecting group" refers to a substituent which protects hydroxyl groups against undesirable reactions during synthetic procedures. Examples of hydroxy-protecting groups include, but are not limited to, ethers, for example, methyl, ethyl, t-butyl, benzyl and allyl; substituted methyl ethers, for example, methoxymethyl, benzyloxymethyl, 2-methoxyethoxymethyl, 2-(trimethylsilyl)-ethoxymethyl, and triphenylmethyl; substituted ethyl ethers, for example, 2,2,2-trichloroethyl and t-butyl; tetrahydropyranyl ethers; silyl ethers, for example, trimethylsilyl, t-butyldimethylsilyl and t-butyldiphenylsilyl; esters, for example, formate, acetate, trifluoroacetate, pivalate, benzoate, and adamantoate; carbonates, for example, methyl, ethyl, isobutyl, t-butyl, vinyl, allyl, and benzyl; sulfonates, for example, methanesulfonate, benzylsulfonate and p-toluenesulfonate. Commonly used hydroxy-protecting groups are disclosed in Greene, T. W., & Wuts, P. G. M. (1991). *Protectective Groups In Organic Synthesis* (2nd ed.). New York: John Wiley & Sons.

The term "oxo" refers to (=O).

The term "perfluoroalkyl" refers to a straight or branched chain hydrocarbon radical containing from 1-to-6 carbon atoms formed by the removal of a single hydrogen atom and all remaining hydrogen atoms have been replaced with fluorine atoms. Representative examples of "perfluoroalkyl" include but are not limited to trifluoromethyl, pentafluoroethyl and the like.

The term "pharmaceutically acceptable prodrugs" represents those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention can exist as stereoisomers where asymmetric or chiral centers are present. These compounds are designated by the symbols "R" or "S," depending on the configuration of substitiuents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Determination of Biological Activity Protein Farnesyltransferase Inhibition

The ability of the compounds of the invention to inhibit protein farnesyltransferase or protein geranylgeranyltransferase can be measured according to the method of Moores, et al., J. Biol. Chem. 266: 14603 (1991), hereby incorporated by reference, or the method of Vogt, et al., J. Biol. Chem. 270:660–664 (1995), hereby incorporated by reference. In addition, procedures for determination of the inhibition of farnesylation of the oncogene protein Ras are described by Goldstein, et al., J. Biol. Chem., 266:15575–15578 (1991), hereby incorporated by reference, and by Singh in U.S. Pat. No. 5,245,061, hereby incorporated by reference.

In addition, in vitro inhibition of protein farnesyltransferase may be measured by the following procedure. Rat brain protein farnesyltransferase activity is measured using an Amersham Life Science commercial scintillation proximity assay kit and substituting a biotin-K Ras B fragment (biotin-Lys-Lys-Ser-Lys-Thr-Lys-Cys-Val-Ile-Met—$CO_2H$), 0.1 mM final concentration, for the biotin-lamin substrate provided by Amersham. The enzyme is purified according to Reiss, Y., et al., Cell, 62: 81–88 (1990), hereby incorporated by reference, utilizing steps one through three. The specific activity of the enzyme is approximately 10 nmol substrate farnesylated/mg enzyme/hour. The percent inhibition of the farnesylation caused by the compounds of the invention (at $10 \times 10^{-6}$ M) compared to an uninhibited control sample is evaluated in the same Amersham test system.

The % inhibition of protein farnesyltransferase was determined for representative compounds of the invention. The results are summarized in Table 1.

TABLE 1

| Example Number | % inhibition at $1 \times 10^{-7}$ M |
|---|---|
| 1 | 100 |
| 2 | 43 |
| 3 | 100 |
| 4 | 55 |
| 5 | 94 |
| 6 | 90 |
| 7 | 100 |
| 8 | 80 |
| 9 | 78 |
| 10 | 63 |
| 11 | 89 |
| 12 | 92 |
| 13 | 92 |
| 14 | 78 |
| 15 | 100 |
| 16 | 100 |
| 17 | 100 |
| 18 | 72 |
| 19 | 75 |
| 20 | 93 |
| 21 | 100 |
| 22 | 100 |
| 23 | 83 |
| 24 | 81 |
| 25 | 86 |
| 26 | 75 |
| 27 | 100 |
| 28 | 100 |

Additional methods for the measurement of in vitro inhibition of protein prenylation (i.e., inhibition of farnesyltransferase or geranygeranyltransferase) are described below.

Assays are performed using the glass fiber filter binding assay procedure with either rabbit reticulocyte lysate or FTase or GGTase I fractions isolated from bovine brains using a combination of hydrophobic and DEAE column chromatography procedures. Protein substrates are purchased from Panvera Corporation (H-ras for FTase, H-ras-CVLL for GGTase I). Tritium labeled prenyl lipid substrates (FPP or GGPP) are obtained from Amersham Life Science.

FTase $^3$H-Farnesyldiphosphate (final concentration 0.6 μM), H-Ras (final concentration 5.0 μM) and the test compound (various final concentrations from a stock solution in 50% DMSO/water; final concentration DMSO <2%) were mixed in buffer (50 mM HEPES (pH 7.5), 30 mM MgCl$_2$, 20 mM KCl, 10 μM ZnCl$_2$, 5 mM DTT, 0.01% Triton X-100) to give a final volume of 50 μL. The mixture was brought to 37° C., enzyme was added, and the reaction is incubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial and 5 mL of scintillation fluid was added. The radioisotope retained on the glass fiber filter was counted to reflect the activity of the enzymes. The IC$_{50}$ value was calculated by measuring the activity of the enzyme over a suitable range of inhibitor concentrations.

GGTase I $^3$H-geranylgeranyldiphosphate (final concentration 0.5 μM), H-Ras-CVLL (final concentration 5.0 μM) and the test compound (various final concentrations from a stock solution in 1:1 DMSO/water; final concentration DMSO <2%) were mixed in buffer (50 mM Tris-HCl (pH 7.2), 30 mM MgCl$_2$, 20 mM KCl, 10 μM ZnCl$_2$, 5 mM DTT, 0.01% Triton X-100) to give a final volume of 50 μL. The mixture was brought to 37° C., treated with enzyme, andincubated for 30 minutes. 1 mL of 1 M HCl/ethanol was added to stop the reaction, and the mixture was allowed to stand for 15 minutes at room temperature then diluted with 2 mL of ethanol. The reaction mixture was filtered through a 2.5 cm glass microfiber filter from Whatman and washed with four 2 mL portions of ethanol. The glass filter was transferred to a scintillation vial, and 5 mL scintillation fluid was added. The radioisotope retained on the glass fiber filter was counted to reflect the activity of the enzymes. The IC$_{50}$ value was calculated by measuring the activity of the enzyme over a suitable range of inhibitor concentrations.

Additionally, the ability of the compounds of the invention to inhibit prenylation in whole cells, inhibit anchorage-independent tumor cell growth and inhibit human tumor xenograft in mice could be demonstrated according to the methods described in PCT Patent Publication No. WO95/25086, published Sep. 21, 1995, which is hereby incorporated herein by reference.

Pharmaceutical Compositions

The compounds of the present invention can be used in the form of pharmaceutically acceptable salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I)–(XII) or separately by reacting the carboxylic acid function with a suitable base such as the hydroxide, carbonate or bicarbonate of a pharmaceutically acceptable metal cation or with ammonia or an organic primary, secondary or tertiary amine. Such pharmaceutically acceptable salts include, but are not limited to, cations based on the alkali and alkaline earth metals such as sodium, lithium, potassium, calcium, magnesium, aluminum salts and the like as well as nontoxic ammonium, quaternary ammonium, and amine cations including, but not limited to, ammonium, tetramethylammonium, tetraethylammonium, methylamine, dimethylamine, trimethylamine, triethylamine, ethylamine and the like. Other representative organic amines useful for the formation of base addition salts include diethylamine, ethylenediamine, ethanolamine, diethanolamine, piperazine and the like.

The compounds of the invention are useful (in humans and other mammals) for inhibiting protein isoprenyltransferases (i.e, protein farnesyltransferase and/or protein geranylgeranyltransferase) and the isoprenylation (i.e., farnesylation and/or geranylgeranylation) of Ras. These inhibitors of protein isoprenyltransferases are also useful for inhibiting or treating cancer in humans and other mammals. Examples of cancers which may be treated with the compounds of the invention include, but are not limited to, carcinomas such as lung, colorectal, bladder, breast, kidney, ovarian, liver, exocrine pancreatic, cervical, esophageal, stomach and small intestinal; sarcomas such as oesteroma, osteosarcoma, lepoma, liposarcoma, hemanioma and hemangiosarcoma; melanomas such as amelanotic and melanotic; mixed types of cancers such as carcinosarcoma, lymphoid tissue type, follicular reticulum, cell sarcoma and Hodgkins disease and leukemias, such as myeloid, acute lymphoblastic, chronic lymphocytic, acute myloblastic and chronic mylocytic.

The ability of the compounds of the invention to inhibit or treat cancer can be demonstrated according to the methods of Mazerska Z., Woynarowska B., Stefanska B., Borowski S., Drugs Exptl. Clin. Res. 13(6), 345–351 (1987) Bissery, M. C., Guenard F., Guerritte-Voegelein F., Lavelle F., Cancer Res. 51, 4845–4852 (1991) and Rygaard J., and Povlsen C., Acta Pathol. Microbiol. Scand. 77, 758 (1969), which are hereby incorporated herein by reference.

These inhibitors of protein isoprenyltransferases are also useful for treating or preventing restenosis in humans and other mammals. The ability of the compounds of the invention to treat or prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993), which are hereby incorporated herein by reference.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

For treatment or prevention of restenosis, the total daily dose administered to a host in single or divided doses may be in amounts, for example, from 0.001 to 1000 mg/kg body weight daily and more preferred from 1.0 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, sublingually, by inhalation spray, rectally or topically in dosage unit formulations containing conventional nontoxic pharmaceutically acceptable carriers, adjuvants, and vehicles. Topical administration may also involve the use of transdermal administration such as transdermal patches or iontophoresis devices. The term parenteral as used herein includes subcutaneous injections, intravenous, intramuscular, intrasternal injection or infusion techniques.

Injectable preparations, for example sterile injectable aqueous or oleagenous suspensions, may be formulated according to the known art using suitable dispersing or wetting and suspending agents. The sterile injectable preparation may also be a sterile injectable solution or suspension in a nontoxic parenterally acceptable diluent or solvent (as in a solution in 1,3-propanediol, for example). Among the acceptable vehicles and solvents that may be employed are water, Ringer's solution and isotonic sodium chloride solution. Additionally, sterile, fixed oils are conventionally employed as a solvent or suspending medium. For this purpose, any bland fixed oil may be employed including synthetic mono- or diglycerides. Fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose, lactose or starch. These dosage forms may also comprise additional substances other than inert diluents such as lubricating agents like magnesium stearate. With capsules, tablets and pills, the dosage forms may also comprise buffering agents. Tablets and pills mayalso be prepared with enteric coatings.

Liquid dosage forms for oral administration may include pharmaceutically acceptable emulsions, solutions, suspensions, syrups and elixirs containing inert diluents commonly used in the art such as water. Such compositions may also comprise adjuvants such as wetting agents, emulsifying and suspending agents and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals dispersed in an aqueous medium. Any non-toxic, physiologically aceptable and metabolizable lipid capable of forming liposomes can be used. The present compositions in liposome form can contain, in addition to a compound of the present invention, stabilizers, preservatives, excipients and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq., which is hereby incorporated herein by reference.

While the compounds of the invention can be administered as the sole active pharmaceutical agent for the treatment of cancer, they can also be used in combination with one or more other chemotherapeutic agents.

Representative examples of chemotherapeutic agents are described in Holleb, et al., *Clinical Oncology*, American Cancer Society, United States (1991) p 56 et seq., which is hereby incorporated herein by reference These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine and vinblastine) and etoposide (VP-16); hormones and hormone antagonists (tamoxifen and corticosteroids); and miscellaneous agents (cisplatin, taxol and brequinar).

The above compounds to be employed in combination with the isoprenyl protein transferase inhibitor of the invention will be used in therapeutic amounts as indicated in the Physicians' Desk Reference (PDR) 47th Edition (1993), which is incorporated herein by reference or by such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied to obtain a desired therapeutic response depending on the route of administration, severity of the disease and the response of the patient.

When administered as a combination, the therapeutic agents can be formulated as separate compositions which are given at the same time or different times, or the therapeutic agents can be given as a single composition.

Abbreviations

Abbreviations that have been used in the descriptions of the scheme and the examples that follow are: $BF_3.OEt_2$ for boron trifluoride diethyl etherate, $Cl_2PdDPPF$ for [1,1'-bis(diphenylphosphino)ferrocene]dichloropalladium (II), DME for 1,2-dimethoxyethane, DMF for N,N- dimethylformamide, DMSO for dimethylsulfoxide, EDC or EDAC or EDCI for 1-ethyl-3-[3-(dimethylamino)propyl]-carbodiimide hydrochloride, HOOBT for 3-hydroxy-1,2,3-benzotriazin-4(3H)-one, and THF for tetrahydrofuran.

Synthetic Methods

The compounds and processes of the present invention will be better understood in connection with the following synthetic schemes which illustrate the methods by which the compounds of the invention can be prepared.

Syntheses of the compounds of the present invention are described in Scheme 1.

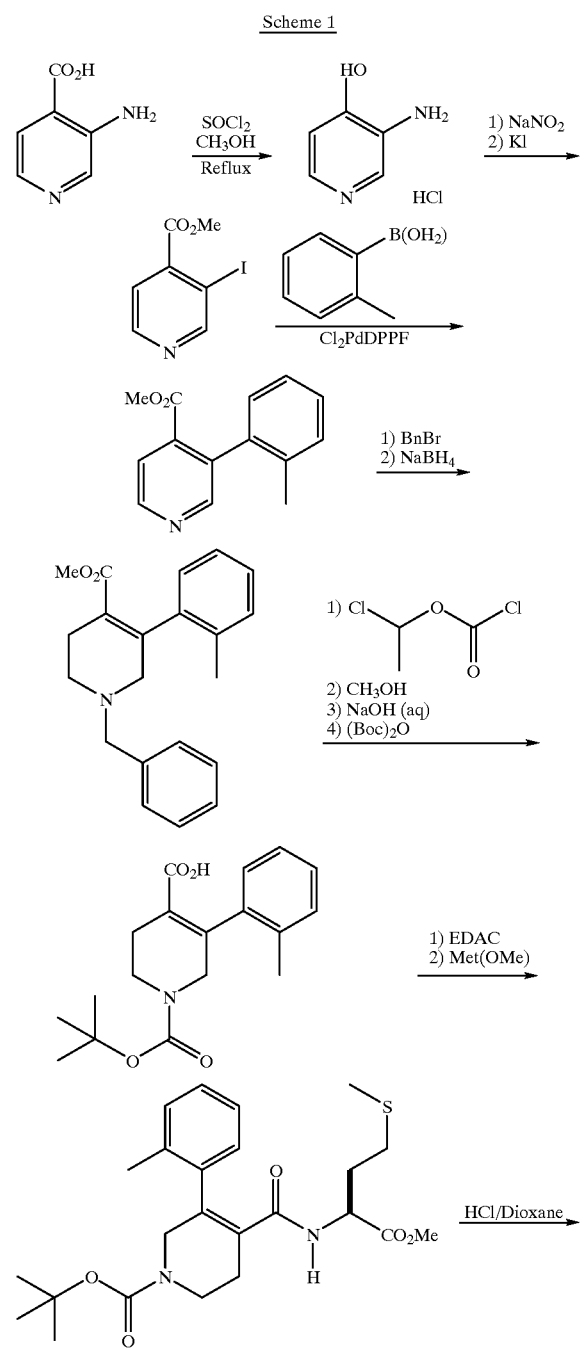

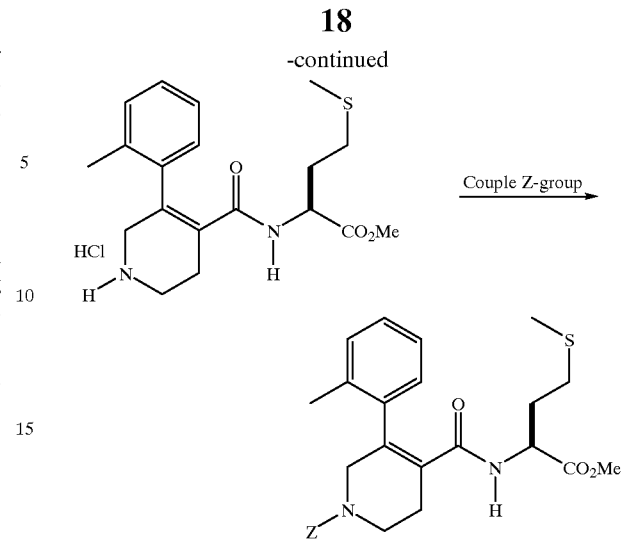

As exemplified in Scheme 1,3-aminoisonicotinic acid was esterified, diazotized, and the diazonium displaced with potassium iodide. A biaryl coupling was accomplished between o-methylphenylboronic acid and 3-iodoisonicotinic acid, methyl ester. Benzyl bromide was used to form the pyridinium cation which was then reduced with sodium borohydride to give a N-benzyltetrahydropyridine derivative. The N-protecting group was replaced with a Boc group and the ester saponified. Methionine methyl ester was coupled to the free carboxylic acid and the Boc group removed to give the amine intermediate. The amine was derivatized using standard alkylation or acylation methods well known to one skilled in the art.

The compounds and processes of the present invention will be better understood in connection with the following examples, which are intended as an illustration of and not a limitation upon the scope of the invention.

EXAMPLE 1

N-4-[1-(3-cyclohexylpropyloxycarbonyl)-3-(2-methylphenyl)-1,2,5,6-tetrahydroisonicotinyl] methionine

EXAMPLE 1A 3-aminoisonicotinic acid, methyl ester

A suspension of 3-aminoisonicotinic acid (13.81 g, 100 mmol, prepared using the procedure described in Crum J. D.; Fuchsman, C. H. *J. Heterocyclic Chem.*, 1966, 3, 252) in methanol (250 mL) was treated with thionyl chloride (14.7 mL, 200 mmol) and heated to reflux for 3 days. The yellow solution was concentrated to dryness to provide a yellow solid. This solid was suspended in 200 mL of ethyl ether and treated with 400 mL of saturated, aqueous $NaHCO_3$ and the biphasic solution was stirred until all of the solids were dissolved. The layers were separated and the aqueous phase was extracted with 2 additional portions of ethyl ether. The combined organic phases were washed with water and brine, dried ($Na_2SO_4$), filtered, and concentrated to provide the title compound as a light yellow solid. MS ($DCI/NH_3$) m/z 153 $(M+H)^+$.

EXAMPLE 1B 3-iodoisonicotinic acid, methyl ester

A cooled (−5° C.) solution of the product from Example 1A (12.37 g, 0.081 mol) in aqueous HCl (100 mL, 3M) and acetone (50 mL) was treated with NaNO$_2$ (6.18 g, 0.089 mol) dissolved in water (40 mL) such that the temperature of the solution was maintained below 0° C. After 2 hours of stirring, the solution was treated with urea (2.39 g, 40 mmol) followed (after 5 minutes) by a solution of KI (24.27 g, 0.146 mol) in water (50 mL) such that the internal temperature did not rise above 2° C. After stirring for 1 hour at 0° C. and 1 hour at room temperature, the solution was treated sequentially with K$_2$CO$_3$ (ca. 15 g) and NaHSO$_3$ (ca.15 g) and stirred for another 30 minutes. The mixture was poured into a separatory funnel and extracted with ether (3×200 mL). The combined organic extracts were extracted with water (100 mL), 20% aqueous Na$_2$SO$_3$ (100 mL), and brine (100 mL), dried (Na$_2$SO$_4$), filtered, and concentrated. The residue was purified by column chromatography on silica gel to provide the title compound.
MS (DCI/NH$_3$) m/z 250 (M+H)$^+$.

EXAMPLE 1C 3-(2-methylphenyl) isonicotinic acid, methyl ester

A mixture of the product from Example 1B (13.14 g, 50 mmol) in degassed DME was treated with ortho-methylphenylboronic acid (7.43 g, 55 mmol), cesium fluoride (1 5.19 g, 100 mmol), and Cl$_2$PdDPPF.CH$_2$Cl$_2$ (1.22 g, 1.50 mmol) and heated to reflux for 3 hours. After cooling to room temperature, the mixture was diluted with ethyl ether (500 mL) and filtered through a 1"×3" pad of activated alumina. The pad was washed with ether (2×100 mL) and the filtrate concentrated to provide 11.12 g (98%) of the title compound as an orange oil. MS (DCI/NH$_3$) m/z 228 (M+H)$^+$.

EXAMPLE 1D 1-benzyl-3-(2-methylphenyl)-1,2,5,6-tetrahydroisonicotinic acid, methyl ester The product from Example 1C (3.54 g, 15.6 mmol) and benzyl bromide (1.9 mL, 16.4 mmol) were heated to 95° C. for 2 hours. After cooling to ambient temperature, the glassy solid was dissolved in methanol (20 mL) and added to a cold (−10° C.) solution of sodium cyanoborohydride in 40 mL of methanol and 8 mL of acetic acid. The mixture was stirred for 72 hours during which time the bath melted. The mixture was diluted with 50 mL of methylene chloride and 50 mL of 2M aqueous sodium carbonate and vigorously stirred for 30 minutes. The layers were separated and the aqueous phase was extracted with 2 portions of methylene chloride. The combined organic phases were dried (Na$_2$SO$_4$), filtered, and concentrated. The residue was purified by flash chromatography on SiO$_2$, 15% ethyl acetate/hexanes to provide 3.48 g (69%) of the title compound as a clear oil.
MS (DCI/NH$_3$) m/z 322 (M+H)$^+$.

EXAMPLE 1E 3-(2-methylphenyl)-1,2,5,6-tetrahydroisonicotinic acid, methyl ester hydrochloride A solution of the product from Example 1D (3.43 g, 10.7 mmol) in 1,2-dichloroethane (20 mL) was treated with l-chloroethylchloroformate (1.4 mL, 12.8 mmol) and the mixture heated to reflux for 4 hours. Methanol (5 mL) was carefully added to the mixture and heating continued for 2 hours. The mixture was allowed to cool to room temperature and concentrated to an orange oil. This oil was triturated with ether to provide a thick oily solid that was placed under a high vacuum overnight. The resulting foam was triturated again with ethyl ether and filtered to provide 2.60 g (91%) of the title compound as a cream-colored solid.
MS (DCI/NH$_3$) m/z 232 (M+H)$^+$.

EXAMPLE 1F 1-(1',1'-dimethylethoxycarbonyl)-3-(2-methylphenyl)-1,2,5,6-tetrahydroisonicotinic acid A solution of the product from Example 1D (5.90 g, 18.35 mmol) in 1,2-dichloroethane (25 mL) was treated with 1-chloroethylchloroformate (4.0 mL, 36.70 mmol), heated to reflux for 4 hours, cooled to ambient temperature, and concentrated. The residue was suspended in concentrated aqueous HCl (25 mL), heated to reflux for 4 hours, cooled to room temperature, and extracted with ethyl acetate. The ethyl acetate was extracted with water and the combined aqueous extracts were adjusted to pH >10 with solid NaOH (ca. 9 g), and with external cooling, applied to control the exotherm. The basic solution was again extracted with ethyl acetate and the aqueous layer was diluted with THF (25 mL), and di-tert-butyldicarbonate (4.00 g, 18.35 mmol) was added. The mixture was stirred overnight, poured into a separatory funnel, and extracted with ether. The combined organic extracts were washed sequentially with 1 M aqueous NaOH (25 mL) and water, and all of the aqueous phases were combined. The pH of the combined aqueous phases was adjusted to 3.5 with aqueous 1M phosphoric acid and extracted with ethyl acetate. The combined organic extracts were extracted with brine, dried (Na$_2$SO$_4$), and concentrated to provide 4.54 g (78%) of the title compound as a viscous yellow oil.
MS (DCI/NH$_3$) m/z 318 (M+H)$^+$.

EXAMPLE 1G

N-4-[1-(1',1'-dimethylethoxycarbonvl)-3-(2-methylphenyl)-1,2,5,6-tetrahydroisonicotinyl] methionine methyl ester The product from Example 1F (4.54 g, 14.30 mmol), 1-ethyl-3-[3-(dimethylamino)propyl]-carbodiimide hydrochloride (3.02 g, 15.73 mmol), HOOBt (2.56 g, 15.73 mmol) and methionine methyl ester hydrochloride (3.55 g, 18.59 mmol) were stirred in 40 mL of DMF until a clear solution resulted. The solution was treated with triethylamine (3.6 mL, 25.74 mmol) and the resulting yellow suspension stirred overnight. The mixture was diluted with water (100 mL) and ethyl acetate (100 mL), and vigorously stirred until two clear phases resulted. The mixture was poured into a separatory funnel and the layers separated. The aqueous phase was extracted with ethyl acetate (2×100 mL) and the combined organic phases were back-extracted with 1 M aqueous NaOH (2×50 mL), water (2×50 mL), and brine. The yellow solution was dried (MgSO$_4$), filtered, and concentrated to provide 6.62 g (100%) of the title compound as a yellow syrup.
MS (ESI(+)) m/z 449 (M+H)$^+$, (ESI(−)) 447 (M−H)$^-$.

EXAMPLE 1H

N-3-(2-methylphenyl)-1,2,5,6-tetrahydroisonicotinyl]methionine, methyl ester hydrochloride The product from Example 1G (6.62 g, 14.3 mmol) was treated with HCl (4N in dioxane, 15 mL) and stirred at room temperature for 36 hours. The solution was concentrated and the residue dissolved in methylene chloride (50 mL). Hexane was added until the solution became cloudy and the mixture concentrated. This process was repeated twice more to provide the title compound as a brown solid.
MS (ESI(+)) m/z 349 (M+H)$^+$, (ESI(−)) 347 (M−H)$^−$.

EXAMPLE 1I tetrahydroisonicotinyl]methionine, methyl ester

A solution of 3-cyclohexyl-1-propanol (63 mL, 0.41 mmol) in 1,2-dichloroethane (4 mL) at −10° C. was treated with 4-methylmorpholine (0.048 mL, 0.44 mmol) followed by 4-nitrophenylchloroformate (83 mg, 0.41 mmol). The cold bath was removed and the mixture was stirred for 4 hours. The solution was treated with 4-methylmorpholine (0.048 mL, 0.44 mmol), followed by the product from Example 1H, and the mixture was stirred overnight. The yellow reaction mixture was poured into ethyl ether (50 mL) and extracted with water (25 mL), 2M aqueous sodium carbonate (3×25 mL), again with water (25 mL), and finally with brine. The ether layer was dried (Na$_2$SO$_4$), filtered, and concentrated. The residue was purified by column chromatography on SiO$_2$ (40% ethyl acetate/hexanes) to provide 101 mg (50%) of the title compound as a light yellow syrup.
MS (ESI(+)) m/z 531 (M+H)$^+$, (ESI(−)) 529 (M−H)$^−$.

EXAMPLE 1J

N-4-[1-(3-cyclohexylpropyloxycarbonyl)-3-(2-methylphenyl)-1,2,5,6-tetrahydroisonicotinyl]methionine To a stirred solution of the product from Example 1 I (95 mg, 0.18 mmol) in THF (1.5 mL) at 0° C. was added LiOH (0.36 mL of a 1M solution, 0.36 mmol) followed by methanol (0.5 mL) and the resulting solution stirred overnight and concentrated to dryness. The residue was dissolved in water and the pH of the solution adjusted to 1 with 3N aqueous HCl. The mixture was extracted with ethyl acetate (3×15 mL) and the combined organic extracts were washed with water (15 mL) and brine. The ethyl acetate layer was dried (Na$_2$SO$_4$), filtered, and concentrated. The residue was lyophilyzed to provide 75 mg of the title compound as a white lyophilate.
$^1$H NMR (300 MHz, DMSO-d$_6$) δ 7.52, bs, 1H; 7.04–7.26, m, 3H; 3.97–4.12, m, 3H; 3.36–3.90, m, 4H; 2.10–2.49, m, 4H; 1.88, s, 3H; 1.52–1.77, m, 9H; 1.09–1.30, m, 6H; 0.74–0.94, m, 2H; MS (ESI(−)) m/z 515 (M−H)$^−$; Anal. calc'd for C$_{28}$H$_{40}$N$_2$O$_5$S.0.28 H2O: C, 64.46; H, 7.84; N, 5.37. Found: C, 64.46; H, 7.62; N, 5.34.

EXAMPLE 2

N-4-[1-(3-[5-thiazolyl]acryloyl)-3-(2-methylphenyl)-1,2,5,6-tetrahydroisonicotinyl]methionine

EXAMPLE 2A

N-4-[1-(3-[5-thiazolyl]acryloyl)-3-(2-methylphenyl)-1,2,5,6-tetrahydroisonicotinyl]methionine, methyl ester A solution of the product from Example 1H (150 mg, 0.38 mmol), EDCI (80 mg, 0.41 mmol), DMAP (12 mg, 0.1 mmol) and 5-thiazolacrylic acid, TFA (127 mg, 0.49 mmol) in DMF (2 mL) was treated with triethylamine (0.152 mL, 1.06 mmol) and stirred for 72 hours. The mixture was poured into 2M aqueous Na$_2$CO$_3$ and extracted with 2 portions of ethyl acetate. The combined organic phases were extracted with 2M aqueous Na$_2$CO$_3$, water and brine, dried (Na$_2$SO$_4$), filtered, and concentrated. The residue was purified by column chromatography on silica gel (ethyl acetate) to provide 72 mg of the title compound.
MS (ESI(+)) m/z 500 (M+H)$^+$, (ESI(−)) 498 (M−H)$^−$.

EXAMPLE 2B

N-4-[1-(3-[5-thiazolyl]acrylovl)-3-(2-methylphenyl)-1,2,5,6-tetrahydroisonicotinyl]methionine Following the procedure for Example 1J, the product from Example 2A (68 mg, 0.13 mmol) provided 53 mg of the title compound as a yellow solid.
$^1$H NMR (300 MHz, DMSO-d$_6$) δ 9.13, d, 1H; 8.28, s, 1H; 8.03, dd, 1H; 7.85, dd, 1H; 7.02–7.29, m, 4H; 4.17, m, 1H; 3.99, m, 1H; 3.63–3.80, m, 1H; 3.18–3.36, m, 2H; 2.30, m, 4H; 1.90–2.11, m, 4H; 1.87, s, 3H; 1.50–1.83, m, 2H; MS (ESI(−)) m/z 484 (M−H)$^−$; Anal. calc'd for C$_{24}$H$_{27}$N$_3$O$_4$S$_2$: C, 59.37; H, 5.60; N, 8.65. Found: C, 59.06; H, 5.54; N, 8.38.

EXAMPLE 3

N-4-[1-(N'-benzyl-5-thiazolmethylaminocarbonyl)-3-(2-methylphenyl)-1,2,5,6-tetrahydroisonicotinyl]methionine

EXAMPLE 3A

N-benzyl-N-5-thiazolemethylamine

Following the procedure for Example 8A, N-benzylamine and 5-thiazolecarboxaldehyde provided the title compound.
MS (DCI/NH$_3$) m/z 205 (M+H)$^+$.

EXAMPLE 3B

N-4-[1-(N'-benzyl-5-thiazolmethylaminocarbonyl)-3-(2-methylphenyl)-1,2,5,6-tetrahydroisonicotinyl]methionine, methyl ester A solution of the product from Example 3A (408 mg, 2 mmol) in toluene (4 mL) was cooled to 0° C. and treated with 4N aqueous NaOH (2 mL). The biphasic mixture was vigorously stirred while phosgene (1.1 mL of a 1.93M toluene solution, 2 mmol) was added dropwise. The cold bath was removed and the mixture stirred for 30 minutes after which an additional phosgene (0.5 mL) was added. After 15 minutes of stirring, the mixture was poured into a separatory funnel and the aqueous phase removed. The toluene layer was removed, dried (K$_2$CO$_3$), filtered, and concentrated to provide an orange oil. A portion of this material was used in the next step. A solution of the product from Example 1H (150 mg, 0.38 mmol) in 1,2-dichloroethane (3 mL) was treated with diisopropylethylamine (0.20 mL, 1.14 mmol) followed by the above carbamoyl chloride (152 mg, 0.57 mmol) and the solution stirred for 1 hour. The yellow mixture was diluted with ethyl acetate and washed successively with water, 3N aqueous HCl, brine, and dried (Na$_2$SO$_4$), filtered, and concentrated. The residue was purified by chromatography on silica gel (ethyl acetate) to provide 155 mg (69%) of the title compound.
MS (ESI(−)) m/z 591 (M−H)$^−$.

EXAMPLE 3C

N-4-[1-(N'-benzyl-5-thiazolmethylaminocarbonyl)-3-(2-methylphenyl)-1,2,5,6-tetrahydroisonicotinyl]methionine Following the procedure for Example 1J, the product from Example 3B was converted to the title compound.

1H NMR (300 MHz, DMSO-$d_6$) δ 8.97, s, 1H; 7.68, s, 1H; 7.35, m, 2H; 7.29, m, 3H; 7.19, m, 4H; 4.52, d, 2H; 4.38, d, 2H; 4.24, m, 1H; 3.97–4.08, m, 1H;, 3.89, m, 1H; 3.66, m, 1H; 3.50, m, 1H; 2.46–2.71, m, 3H; 2.22, m, 3H; 1.92, s, 3H; 1.44–1.90, m, 4H; MS (ESI(–)) m/z 577 (M–H)$^-$; Anal. calc'd for $C_{29}H_{34}N_4O_5S_3$: C, 56.66; H, 5.57; N, 9.11. Found: C, 56.91; H, 56.91; H, 5.62; N, 8.95.

EXAMPLE 4

N-[N'-(3-phenylpropyl)-3-(2-methylphenyl)-1,2,5,6-tetrahydroisonicotinyl]methionine

EXAMPLE 4A

N-(3-phenylpropyl)-3-(2-methylphenyl)-1,2,5,6-tetrahydroisonicotinic acid methyl ester A solution of the product from Example 1E (173 mg, 0.5 mmol) and hydrocinnamaldehyde (212 mg, 1.0 mmol) in 3 mL of 1,2-dichloroethane was treated with triethylamine (0.070 mL, 0.5 mmol) followed by sodium triacetoxyborohydride (422 mg, 2.0 mmol) and the mixture stirred overnight. The mixture was treated with 0.3 mL of acetic acid and after stirring 2 hours, quenched by the careful addition of saturated, aqueous $NaHCO_3$. The mixture was diluted with saturated, aqueous $NaHCO_3$ and extracted with 2 portions of methylene chloride. The combined organic phases were dried ($Na_2SO_4$), filtered, and concentrated. The residue was dissolved in ether and treated with excess HCl in ethyl acetate. The organic phase was diluted with hexanes and extracted with water until TLC analysis indicated no amine present in the organic phase. The combined aqueous extracts were made basic with solid $NaHCO_3$ and extracted with 3 portions of ethyl ether. The combined ether extracts were dried ($Na_2SO_4$), filtered, and concentrated to provide 164 mg (90%) of the title compound as a yellow oil.
MS (DCI/$NH_3$) m/z 350 (M+H)$^+$.

EXAMPLE 4B

N-(3-phenylpropyl)-3-(2-methylphenyl)-1,2,5,6-tetrahydroisonicotinic acid

A solution of the product from Example 4A (157 mg, 0.43 mmol) in 3 mL of ethanol was treated with 1 mL of 4N aqueous sodium hydroxide. The resulting solution was stirred for 1 hour at room temperature and at reflux for 30 minutes and allowed to cool to room temperature and concentrated. The residue was dissolved in water and the pH of the solution adjusted to ca.4 by the addition of 0.5M aqueous phosphoric acid. The solution was saturated with sodium chloride and extracted with 5 portions of ethyl acetate. The combined organic phases were dried ($Na_2SO_4$), filtered, and concentrated to provide 121 mg (84%) of the title compound.
MS (DCI/$NH_3$) m/z 336 (M+H)$^+$.

EXAMPLE 4C

N-[N'-(3-phenylpropyl)-3-(2-methylphenyl)-1,2,5,6-tetrahydroisonicotinyl]methionine, methyl ester Following the procedure for Example 1G, the product from Example 4B (116 mg, 0.33 mmol) was converted to 129 mg (81%) of the title compound.
MS (DCI/$NH_3$) m/z 481 (M+H)$^+$.

EXAMPLE 4D

N-[N'-(3-phenylpropyl)-3-(2-methylphenyl)-1,2,5,6-tetrahydroisonicotinyl]methionine Following the procedure for Example 1J, the product from Example 4C (123 mg, 0.26 mmol) was converted to the title compound.

1H NMR (300 MHz, DMSO-$d_6$) δ 7.07–7.43, m, 10H; 4.07, m, 1H; 2.55–3.30, m, 8H; 2.19, bs, 3H; 1.88, s, 3H; 1.82, m, 4H; 1.70, m, 1H; 1.51, m, 1H; MS (DCI/$NH_3$) m/z 467 (M+H)$^-$; Anal. calc'd for $C_{27}H_{34}N_2O_3S$.0.96 H2O: C, 67.01; H, 7.48; N, 6.05. Found: C, 67.01; H, 6.97; N, 5.64.

EXAMPLE 5

N-[N'-(3-pyridylacetyl)-3-(2-methylphenyl)-1,2,5,6-tetrahydroisonicotinyl]methionine

EXAMPLE 5A

N-(3-pyridylacetyl)-3-(2-methylphenyl)-1,2,5,6-tetrahydroisonicotinic acid ethyl ester A solution of the product from Example 1E (123 mg, 0.5 mmol) in 2 mL of DMF was treated with 3-pyridyl acetic acid hydrochloride (132 mg. 0.75 mmol), EDC (105 mg, 0.55 mmol), HOOBt (90 mg, 0.55 mmol), and triethylamine (0.21 mL, 1.5 mmol), and the resulting suspension stirred vigorously for 48 hours. The work-up of Example 1G was followed providing the crude product. This product was purified by flash column chromatography on silica gel 80/20 ethyl acetate/hexanes to provide 117 mg (64%) of the title compound as a colorless oil.
MS (DCI/$NH_3$) m/z 351 (M+H)$^+$.

EXAMPLE 5B

N-(3-pyridylacetyl)-3-(2-methylphenyl)-1,2,5,6-tetrahydroisonicotinic acid, methyl ester Following the procedure for Example 4B, the product from Example 5A (118 mg, 0.32 mmol) was converted to 81 mg (76%) of the title compound.
MS (DCI/$NH_3$) m/z 337 (M+H)$^+$.

EXAMPLE 5C

N-[N'-(3-pyridylacetyl)-3-(2-methylphenyl)-1,2,5,6-tetrahydroisonicotinyl]methionine methyl ester Following the procedure for Example 1G, the product from Example 5B (75 mg, 0.22 mmol) was converted to 86 mg (81%) of the title compound.
MS (ESI(+)) m/z 482 (M+H)$^+$, (ESI(–)) 480 (M–H)$^-$.

EXAMPLE 5D

N-[N'-(3-pyridylacetyl)-3-(2-methylphenyl)-1,2,5,6-tetrahydroisonicotinyl]methionine Following the procedure for Example 1J, the product from Example 5C (82 mg, 0.17 mmol) was converted to 70 mg (88%) of the title compound.
1H NMR (300 MHz, DMSO-$d_6$) δ 8.44, m, 2H; 8.05, m, 1H; 7.63, m, 1H; 7.34, m, 1H; 7.02–7.20, m, 3H; 6.90, d, 1H; 4.17, m, 1H; 3.75–4.04, m, 3H; 3.35–3.56, m, 3H; 2.17–2.38, m, 4H; 1.91–2.05, m, 3H; 1.90, s, 3H; 1.77, m, 1H; 1.59, m, 1H; MS (ESI(+)) m/z 468 (M+H)$^+$, 490 (M+Na)+, (ESI(–)) 466 (M–H)$^-$; Anal. calc'd for $C_{25}H_{31}N_3O_4S$: C, 63.94; H, 6.65; N, 8.95. Found: C, 63.75; H, 6.31; N, 8.55.

EXAMPLE 6

N-4-[1-(N'-benzyl-5-thiazolmethylaminosulfamoyl)-3-(2-methylphenyl)-1,2,5,6-tetrahydroisonicotinyl]methionine

EXAMPLE 6A

N-4-[1-(N'-benzyl-5-thiazolmethylaminosulfamoyl)-3-(2-methylphenyl)-1,2,5,6-tetrahydroisonicotinyl]methionine, methyl ester A solution of the product from Example 3A (408 mg, 2 mmol) in dichloromethane (4 mL) was cooled to –10° C.

and treated with Hunigs' base (0.70 mL, 4 mmol) followed by a solution of sulfuryl chloride (0.16 mL, 2 mmol) in 5 mL of dichloromethane. After 1 hour of stirring, the mixture was treated with an additional 0.16 mL of sulfuryl chloride and stirred for an additional hour. The solution was diluted with ethyl ether, washed with 2 portions of 2N sodium hydroxide solution, dried ($Na_2SO_4$), filtered, and concentrated to provide a brown oil that was used directly. A solution of Example 1H (150 mg, 0.38 mmol) in 1,2-dichloroethane (3 mL) was treated with diisopropylethylamine (0.20 mL, 1.14 mmol) followed by the above sulfamoyl chloride (172 mg, 0.57 mmol) and the solution stirred for 1 hour. The yellow mixture was diluted with ethyl acetate and washed successively with water, 3N aqueous HCl, brine, dried ($Na_2SO_4$), filtered, and concentrated. The residue was purified by chromatography on silica gel (ethyl acetate/hexanes) to provide 72 mg (30%) of the title compound.
MS (APCI(+)) m/z 629 (M+H)$^+$.

EXAMPLE 6B

N-4-[1-(N'-benzyl-5-thiazolmethylaminosulfamoyl)-3-(2-methylphenyl)-1,2,5,6-tetrahydroisonicotinyl]methionine Following the procedure for Example 1J, the product from Example 6A provided the title compound.
$^1$H NMR (300 MHz, DMSO-d$_6$) δ 12.55, bs, 1H; 9.01, s, 1H; 7.69, s, 1H; 7.23–7.38, m, 5H; 7.09–7.22, m, 5H; 4.56, s, 2H; 4.33, s, 2H; 4.08, m, 1H; 3.72, d, 1H; 3.59, d, 1H; 3.3–3.52, m, 2H; 2.10–2.64, m, 7H; 1.88, s, 3H; 1.69, m, 1H; 1.52, m, 1H; MS (APCI(+)) m/z 615 (M+H)$^-$; Anal. calc'd for $C_{29}H_{34}N_4O_5S_3$: C, 56.66; H, 5.57; N, 9.11. Found: C, 56.91; H, 5.62; N, 8.95.

EXAMPLE 7

N-4-[1-N'-(2-benzyl-2-(4-thiazolylmethyl) glycinovl)-3-(2-methylphenyl)-1,2,5,6-tetrahydroisonicotinyl]methionine

EXAMPLE 7A

N-benzyl-N-4-thiazolemethylamine

Following the procedure for Example 8A, benzyl amine and 4-thiazolecarboxaldehyde provided the title compound.
MS (DCI/NH$_3$) m/z 205 (M+H)$^+$.

EXAMPLE 7B

N-4-[1-N'-(2-benzyl-2-(4-thiazolylmethyl) aminoacetyl)-3-(2-methylphenyl)-1,2,5,6-tetrahydroisonicotinyl]methionine, methyl ester Following the procedure for Example 9A, the products from Example 1H and Example 7A provided the title compound.
MS (ESI(+)) m/z 607 (M+H)$^+$, (ESI(−)) 605 (M−H)$^-$.

EXAMPLE 7C

N-4-[1-N'-(2-benzyl-2-(4-thiazolylmethyl) glvcinoyl)-3-(2-methylphenyl)-1,2,5,6-tetrahydroisonicotinyl]methionine Following the procedure for Example 1J, the product from Example 7B provided the title compound.
$^1$H NMR (300 MHz, DMSO-d$_6$) δ 12.58, bs, 1H; 9.10, s, 1H; 8.90, s, 1H; 7.58, s, 1H; 7.00–7.49, m, 9H; 3.90–4.15, m, 3H; 3.50–3.88, m, 6H; 2.07–2.40, m, 5H; 1.79, 2.00, m, 5H; 1.69, m, 1H; 1.52, m, 1H; MS (ESI(+)) m/z 593 (M+H)$^+$, 615 (M+Na)$^-$, (ESI(−)) 591 (M−H)$^-$; Anal. calc'd for $C_{31}H_{36}N_4O_4S_2$·0.56 H2O: C, 61.76; H, 6.21; N, 9.09. Found: C, 61.85; H, 6.23; N, 8.82.

EXAMPLE 8

N-4-[1-N'-(2-benzyl-2-(4-thiazolylmethyl) aminoacetyl)-3-(2-methylphenyl)-1,2,5,6-tetrahydroisonicotinyl]methionine

EXAMPLE 8A

N-benzyl-N-2-thiazolylmethylamine

A stirred solution of N-benzylamine (0.56 mL, 5.1 mmol) and 2-thiazolecarboxaldehyde (0.55 g, 4.9 mmol) in toluene was heated to reflux for 2 hours with azeotropic removal of water. The solution was cooled to room temperature and concentrated to an oil. This oil was dissolved in 15 mL of ethanol and treated with excess NaBH$_4$ and the mixture stirred overnight. Acetone was added and the mixture stirred 30 minutes and concentrated to a soild mass. This mass was partitioned between 2N aqueous NaOH and 2 portions of ethyl ether. The combined ethereal extracts were washed with water, brine, dried ($Na_2SO_4$), filtered, and concentrated. The residue was purified by flash column chromatography on silica gel to provide 0.59 g (57%) of the title compound.
MS (DCI/NH$_3$) m/z 205 (M+H)$^+$.

EXAMPLE 8B

N-benzyl-N-2-thiazolylmethylchloroacetamide

A stirred solution of N-benzyl-N-2-thiazolylmethylamine (204 mg, 1.0 mmol) in 5 mL of dichloromethane was cooled to 0° C. The solution was treated with 5 mL of saturated, aqueous NaHCO$_3$ followed by the addition of chloroacetyl chloride (0.088 mL, 1.1 mmol). The biphasic mixture was stirred vigorously for 1 hour and poured into a separatory funnel. The layers were separated and the aqueous layer extracted with an additional 5 mL portion of dichloromethane. The combined organic phases were dried ($Na_2SO_4$), filtered, and concentrated to provide the title compound which was used in the next step without further purification.

EXAMPLE 8C

N-4-[1-N'-(2-benzyl-2-(4-thiazolylmethyl) aminoacetyl)-3-(2-methylphenyl)-1,2,5,6-tetrahydroisonicotinyl]methionine, methyl ester A suspension of the products from Example 1H (150 mg, 0.38 mmol) and Example 8B (128 mg, 0.46 mmol) in 3 mL of acetonitrile was treated with Hunigs' base (0.39 mL, 0.86 mmol) and tetrabutylammonium iodide (170 mg, 0.46 mmol) and the mixture was stirred at ambient temperature for 18 hours. The yellow-orange solution was diluted with ethyl acetate, poured into a separatory funnel, and extracted with ½ saturated, aqueous NaHCO$_3$. The aqueous phase was extracted with 2 additional portions of ethyl acetate and the combined organic phases were washed with 2 portions of brine, dried ($Na_2SO_4$), filtered, and concentrated. The residue was purified by column chromatography (silica gel, ethyl acetate) to provide 176 mg (76%) of the title compound.
MS (ESI(+)) m/z 607 (M+H)$^+$, (ESI(−)) 605 (M−H)$^-$.

EXAMPLE 8D

N-4-[1-N'-(2-benzyl-2-(4-thiazolylmethyl)
aminoacetyl)-3-(2-methylphenyl)-1,2,5,6-
tetrahydroisonicotinyl]methionine Following the procedure for Example 1J, the product from Example 8C provided the title compound.

$^1$H NMR (300 MHz, DMSO-$d_6$) δ 7.80, d, ½H; 7.71, m, 1H; 7.66, d, ½H; 7.25–7.43, m, 5H; 7.20, m, 2H; 7.15, bs, 3H; 4.98, bs, 1H; 4.80, bs, 1H; 4.69, bs, 1H; 4.52, bs, 1H; 4.08, m, 1H; 3.44, d, 2H; 3.18, d, 1H; 3.00, d, 1H; 2.81, m, 1H; 2.70, m, 1H; 2.24–2.62, m, 4H; 2.28, bs, 3H; 1.89, bs, 3H; 1.67, m, 1H; 1.53, m, 1H; MS (ESI(+)) m/z 615 (M+Na)$^-$, 593 (M+H)$^+$, (ESI(−)) 591 (M−H)$^-$; Anal. calc'd for $C_{31}H_{36}N_4O_4S_2$·0.77 EtOAc: C, 61.96; H, 6.43; N, 8.48. Found: C, 61.56; H, 6.12; N, 8.91.

EXAMPLE 9

N-4-[1-N'-(2-benzyl-2-(2-thiazolylmethyl)
aminoacetyl)-3-(2-methylphenyl)-1,2,5,6-
tetrahydroisonicotinyl]methionine

EXAMPLE 9A

N-4-[1-N'-(2-benzyl-2-(2-thiazolylmethyl)
aminoacetyl)-3-(2-methylphenyl)-1,2,5,6-
tetrahydroisonicotinyl]methionine, methyl ester A solution of Example 1H (150 mg, 0.38 mmol) in 1 mL of dichloromethane was cooled in an ice bath. The solution was treated with 2 mL of saturated, aqueous NaHCO$_3$ followed by the dropwise addition of chloroacetyl chloride (0.033 mL, 0.40 mmol). The biphasic mixture was vigorously stirred for 10 minutes and diluted with water and dichloromethane. The organic phase was separated, dried (Na$_2$SO$_4$), filtered, and concentrated. The residue was dissolved in 2 mL of acetonitrile and successively treated with the product from Example 8A (85 mg, 0.42 mmol), Hunigs' base (0.10 mL, 0.57 mmol), and tetrabutylammonium iodide (140 mg, 0.38 mmol) and this mixture was stirred for 24 hours at room temperature and 24 hours at 50° C. After cooling to room temperature, the reaction mixture was poured into water and extracted with 3 portions of ethyl acetate. The combined organic phases were washed once with saturated, aqueous NaHCO$_3$, once with water and once with brine, dried (Na$_2$SO$_4$), filtered, and concentrated. The residue was purified by column chromatography (silica gel, ethyl acetate) to provide 138 mg (60%) of the title compound.

MS (ESI(+)) m/z 607 (M+H)$^+$, (ESI(−)) 605 (M−H)$^-$.

EXAMPLE 9B

N-4-[1-N'-(2-benzyl-2-(2-thiazolylmethyl)
aminoacetyl)-3-(2-methylphenyl)-1,2,5,6-
tetrahydroisonicotinyl]methionine Following the procedure for Example 1J, the product from Example 9A was converted to the title compound.
MS (ESI(+)) m/z 593 (M+H)$^+$, 615 (M+Na)$^-$, (ESI(−)) 591 (M−H)$^-$; Anal. calc'd for $C_{31}H_{36}N_4O_4S_2$: C, 62.81; H, 6.12; N, 9.45. Found: C, 62.42; H, 6.14; N, 9.34.

EXAMPLE 10

N-4-[1-(2-[N"-benzyl-N"-2-thiazolylmethyl)
acetamido)-3-(2-methylphenyl)-1,2,5,6-
tetrahydroisonicotinyl]methionine, methyl ester

EXAMPLE 10A

N-benzyl-N-(4-thiazolylmethyl)chloroacetamide

4-Chloromethylthiazole (1.33 g, 10.0 mmol) and benzylamine (2.2 mL, 20.0 mmol) were mixed together and heated to 80° C. for 24 hours and allowed to cool to room temperature. The solid mass was treated with 2M aqueous sodium carbonate and stirred until the mass was broken up and the mixture was extracted with 2 portions of ethyl ether. The combined organic extracts were dried (Na$_2$SO$_4$), filtered, and concentrated. The residue was dissolved in 40 mL of dichloromethane, cooled to 0° C., and 40 mL of saturated, aqueous NaHCO$_3$ was added. To this stirred biphasic mixture was added chloroacetyl chloride (1.8 mL, 22.0 mmol) dropwise and mixture was stirred for an additional 2 hours at 0° C. The layers were separated and the organic phase was dried (Na$_2$SO$_4$), filtered, and concentrated. The residue was purified by column chromatography (silica gel, 30% –50% ethyl acetate/hexanes) to provide first, 0.58 g (21%) N-benzylchloroacetamide followed by 0.76 g (27%) of the title compound.

MS (DCI/NH$_3$) m/z 281($^{35}$Cl) (M+H)$^+$, 283 ($^{37}$Cl) (M+H)$^+$.

EXAMPLE 10B

N-4-[1-(2-[N"-benzyl-N"-2-thiazolylmethyl)
acetamido)-3-(2-methylphenyl)-1,2,5,6-
tetrahydroisonicotinyl]methionine methyl ester A solution of the product from Example 1H (150 mg, 0.38 mmol), the product from Example 10A (129 mg, 0.46 mmol), tetrabutylammonium iodide (170 mg, 0.46 mmol), and Hunigs' base (0.14 mL, 0.76 mmol) in 2 mL of acetonitrile was stirred for 72 hours at room temperature. The mixture was poured into water and extracted with 2 portions of ethyl acetate. The combined organic extracts were washed with 2 portions of water and 1 portion of brine, dried (Na$_2$SO$_4$), filtered, and concentrated. The residue was purified by column chromatography (silica gel, ethyl acetate) to provide the title compound.

MS (ESI(+)) m/z 607 (M+H)$^+$, (ESI(−)) 605 (M−H)$^-$.

EXAMPLE 10C

N-4-[1-(2-[N"-benzyl-N"-2-thiazolylmethyl)
acetamido)-3-(2-methylphenyl)-1,2,5,6-
tetrahydroisonicotinyl]methionine, methyl ester Following the procedure for Example 1J, the product from Example 10B was converted to the title compound.

$^1$H NMR (300 MHz, DMSO-$d_6$) δ 9.11, 9.04, 2-singlets, total 1H; 7.67, s, 1H; 7.09–7.24, m, 10H; 3.50–4.88, m, 8H; 2.21–3.49, m, 6H; 2.06, bs, 3H; 1.90, s, 3H; 1.68, m, 1H; 1.50, m, 1H; MS (ESI(+)) m/z 593 (M+H)$^+$, 615 (M+Na)$^+$, (ESI(−)) 591 (M−H)$^-$; Anal. calc'd for $C_{31}H_{36}N_4O_4S_2$·2.94 H$_2$O: C, 57.66; H, 6.54; N, 8.68. Found: C, 57.54; H, 6.19; N, 8.13.

EXAMPLE 11

N-[4-[(5-(4-chlorophenyl)-2-
methoxycarbonylfuranyl)-3-(2-methylphenyl)-1,2,5,
6-tetrahydroisonicotinyl]methionine

EXAMPLE 11A 5-bromo-2-hydroxymethylfuran

To a solution of 5-bromofuroic acid (8.97 g, 47.0 mmol) in 200 mL of THF at 0° C. was added N-methylmorpholine (5.23 g, 51.7 mmol) followed by isobutyl chloroformate (6.74 g, 49.5 mmol) and the reaction mixture was stirred for 30 minutes at 0° C. Sodium borohydride (10.7 g, 282 mmol) was added followed by 2 mL of saturated, aqueous NaHCO$_3$ and the reaction mixture was stirred for 16 hours. The reaction was quenched with 4 mL of 0.5M phosphoric acid and the reaction was evaporated to a 20 mL volume and extracted with ethyl acetate (3×), dried ($Na_2SO_4$), filtered, and evaporated to an oil. Purification by flash chromatography (50% ethyl acetate/hexanes) provided the title compound as an oil which was unstable to oxygen at ambient temperature.

EXAMPLE 11B 5-(4-chlorophenyl)-2-hydroxymethylfuran

The product from Example 11A (1.012 g, 5.72 mmol) in 10 mL of DMF was treated sequentially with $PdCl_2$ $(PPh_3)_2$ (401 mg, 0.57 mmol), 4-chlorophenylboronic acid (1.78 g, 11.4 mmol), and $Cs_2CO_3$ (3.71 g, 11.4 mmol). The reaction was heated at 80° C. under $N_2$ for 12 hours. The reaction mixture was taken up in ethyl acetate and washed with water (3×) and brine (3×), dried ($Na_2SO_4$), filtered, and evaporated to a brown oil that was purified by flash chromatography (50% ethyl acetate/hexanes) to provide 345 mg (35%) the title compound as an oil.

EXAMPLE 11C

N-[4-[(5-(4-chlorophenyl)-2-methoxycarbonylfuranyl)-3-(2-methylphenyl)-1,2,5,6-tetrahydroisonicotinyl]methionine, methyl ester To a stirred solution of the product from Example 11B (103 mg, 0.49 mmol) in 2 mL of dichloromethane at −10° C. was added 4-methylmorpholine (0.16 mL, 1.44 mmol) and p-nitrophenylchloroformate (91 mg, 0.45 mmol) and the mixture was stirred at −10° C. for 1 hour. The reaction mixture was treated with a solution of Example 1H (164 mg, 0.41 mmol) in 3 mL of dichloromethane, the solution was stirred for 24 hours and poured into water. The phases were separated and the aqueous phase was extracted with 2 portions of ether. The combined organic fractions were extracted with 3 portions of 0.5N sodium hydroxide, water, and brine, dried ($Na_2SO_4$), filtered, and concentrated. The residue was purified by column chromatography (silica gel, 15% ethyl acetate/hexanes) to provide 118 mg (48%) of the title compound.
MS (ESI(+)) m/z 597 (M+H)$^+$, (ESI(−)) 595 (M−H)$^-$.

EXAMPLE 11D

N-[4-[(5-(4-chlorophenyl)-2-methoxycarbonylfuranyl)-3-(2-methylphenyl)-1,2,5,6-tetrahydroisonicotinyl]methionine Following the procedure for Example 1J, the product from Example 11C was converted to the title compound.
$^1$H NMR (300 MHz, DMSO-$d_6$) δ 11.01, s, 1H; 8.12, d, 1H; 7.70, m, 2H; 7.48, m, 3H; 7.14, m, 4H; 6.99, m, 1H; 6.63, bs, 1H; 5.13, s, 2H; 3.42–4.15, 4H; 2.09–2.48, m, 5H; 1.90 (2-singlets), 3H total; 1.71, m, 1H; 1.53, m, 1H; MS (ESI(+)) m/z 583 (M+H)$^+$, (ESI(−)) 581 (M−H)$^-$; Anal. calc'd for $C_{31}H_{31}ClN_2O_6S$.2.30 $H_2O$: C, 57.70; H, 5.75; N, 4.49. Found: C, 57.56; H, 5.36; N, 5.43.

EXAMPLE 12

N-4-[1-N'-(N''-2-cyclhexylethylmethylglycinoyl)-3-(2-methylphenyl)-1,2,5,6-tetrahydroisonicotinyl]methionine

EXAMPLE 12A

N-4-[1-N'-(N''-2-cyclhexylethylmethylglycinoyl)-3-(2-methylphenyl)-1,2,5,6-tetrahydroisonicotinyl]methionine, methyl ester Following the procedure for Example 9A, the product from Example 1H (150 mg, 0.38 mmol) and N-methyl-N-2-cyclohexylethylamine (59 mg, 0.42 mmol) provided 108 mg (57%) of the title compound.
MS (ESI(+)) m/z 544 (M+H)$^+$, (ESI(−)) 542 (M−H)$^-$.

EXAMPLE 12B

N-4-[1-N'-(N''-2-cyclhexylethylmethyllycinoyl)-3-(2-methylphenyl)-1,2,5,6-tetrahydroisonicotinyl]methionine Following the procedure for Example 1J, the product from Example 12A was converted to the title compound.
$^1$H NMR (300 MHz, DMSO-$d_6$) δ 7.00–7.47, m, 5H; 4.00–4.36, m, 3H; 3.40–3.89, m, 4H; 2.11–2.48, m, 10H; 1.97, m, 1H; 1.88, s, 3H; 1.40–1.77, m, 7H; 0.98–1.39, m, 7H; 0.70–0.96, m, 2H; MS (ESI(+)) m/z 530 (M+H)$^+$, (ESI(−)) 528 (M−H)$^-$; Anal. calc'd for $C_{29}H_{43}N_3O_4S$.0.58 $H_2O$: C, 64.48; H, 8.24; N, 7.78. Found: C, 64.48; H, 8.10; N, 7.63.

EXAMPLE 13

N-4-[1-N'-(N''-2-cyclhexylethylmethylaminocarbonyl)-3-(2-methylphenyl)-1,2,5,6-tetrahydroisonicotinyl]methionine

EXAMPLE 13A

N-4-[1-N'-(N''-2-cyclhexylethylmethylaminocarbonyl)-3-(2-methylphenyl)-1,2,5,6-tetrahydroisonicotinyl]methionine, methyl ester Following the procedure for Example 3A, the product from Example 1H (150 mg, 0.38 mmol) and N-methyl-N-2-cyclohexylethylamine (59 mg, 0.42 mmol) provided 134 mg (67%) of the title compound.
MS (ESI(+)) m/z 530 (M+H)$^+$, (ESI(−)) 528 (M−H)$^-$.

EXAMPLE 13B

N-4-[1-N'-(N''-2-cyclhexylethylmethylaminocarbonyl)-3-(2-methylphenyl)-1,2,5,6-tetrahydroisonicotinyl]methionine Following the procedure for Example 1J, the product from Example 13A was converted to the title compound.
$^1$H NMR (300 MHz, DMSO-$d_6$) δ 12.57, bs, 1H; 7.45, m, 1H; 6.97–7.27, m, 4H; 4.09, m, 1H; 3.72, d, 1H; 3.64, d, 1H; 3.20–3.48, m, 2H; 3.15, m, 2H; 2.76, s, 3H; 2.35–2.70, m, 3H; 2.18, m, 3H; 1.88, s, 3H; 1.44–1.77, m, 8H; 1.39, q, 2H; 1.03–1.27, m, 4H; 0.80–0.95, m, 2H; MS (ESI(+)) m/z 516 (M+H)$^+$, (ESI(−)) 514 (M−H)$^-$; Anal. calc'd for $C_{28}H_{41}N_3O_4S$.0.35 $H_2O$: C, 64.43; H, 8.05; N, 8.05. Found: C, 64.43; H, 7.96; N, 7.90.

EXAMPLE 14

N-4-[(N'-2-benzyloxyacetyl)-3-(2-methylphenyl)-1,2,5,6-tetrahydroisonicotinyl]methionine

EXAMPLE 14A

N-4-[(N'-2-benzyloxvacetyl)-3-(2-methylphenyl)-1,2,5,6-tetrahydroisonicotinyl]methionine, methyl ester To a stirred solution of the product from Example 1H (150 mg, 0.38 mmol) in 1 mL of dichloromethane at 0° C. was added 1 mL of 2M aqueous sodium carbonate followed by 0.066 mL of benzyloxyacetyl chloride. After stirring for 30 minutes at 0° C., the bath was removed and the mixture stirred for an additional 30 minutes and quenched by the addition of water. The layers were separated and the aqueous layer was extracted with an additional portion of dichloromethane and the combined organic phases were dried ($Na_2SO_4$), filtered, and concentrated. The residue was purified by column chromatography (silica gel, 70/30 ethyl acetate/hexanes) to provide 133 mg (68%) of the title compound.
MS (ESI(+)) m/z 511 (M+H)$^+$, (ESI(−)) 509 (M−H)$^-$.

EXAMPLE 14B

N-4-[(N'-2-benzyloxyacetyl)-3-(2-methylphenyl)-1, 2,5,6-tetrahydroisonicotinyl]methionine Following the procedure for Example 1J, the product from Example 14A was converted to the title compound.
$^1$H NMR (300 MHz, DMSO-$d_6$) δ 7.28–7.40, m, 6H; 7.05–7.19, m, 4H; 4.48–4.57, m, 3H; 4.18–4.40, m, 3H; 3.44–4.16, m, 3H; 2.14–2.29, m, 5H; 1.91–2.06, m, 2H; 1.88, s, 3H; 1.70, m 1H; 1.55, m, 1H; MS (ESI(+)) m/z 497 (M+H)$^+$, 519 (M+Na)$^-$, (ESI(−)) 495 (M−H)$^-$; Anal. calc'd for $C_{27}H_{32}N_2O_5S \cdot 0.42\ H_2O$: C, 64.32; H, 6.57; N, 5.56. Found: C, 64.32; H, 6.20; N, 5.22.

EXAMPLE 15

N-4-[(N'-2(S)-1-ethylthio-3-cyclohexyl-2-propoxycarbonyl)-3-(2-methylphenyl)-1,2,5,6-tetrahydroisonicotinyl]methionine, lithium salt

EXAMPLE 15A (S)-3-cyclohexyllactic acid

To a solution of (S)-3-phenyllactic acid (20 g) in ethanol (250 mL) was added 5% rhodium on alumina (2.5 g) and the reaction was shaken under 4 atm $H_2$ for 24 hours. The reaction was filtered and concentrated to provide 20 g of the title compound as a white solid.
$^1$H NMR (300 MHz, CDCl$_3$) δ 0.86–1.07, m, 2H; 1.08–1.39, m, 3H; 1.54–1.91, m, 9H; 4.33, dd, J=9.3, 3.6 Hz, 1H; MS (DCI/NH$_3$) m/z 190 (M+NH$_4$)$^+$.

EXAMPLE 15B (S)-3-cyclohexyl-1,2-propanediol

To a solution of the product from Example 15A (15 g) in THF (100 mL) at 0° C. was added 1M BH$_3$-THF (130 mL), and the reaction was warmed to ambient temperature. After 5 hours, the reaction was quenched cautiously with aqueous THF (1: 1, 100 mL), then with 1 M KOH (100 mL). The reaction was concentrated, diluted with water (200 mL), and washed with EtOAc (3×150 mL). The organic extracts were washed with brine (100 mL), dried (MgSO$_4$), filtered, and concentrated to provide 14 g of the title compound as a colorless oil.
$^1$H NMR (300 MHz, CDCl$_3$) δ 0.80–1.04, m, 2H; 1.05–2.00, m, 13H; 3.41, dd, J=10.8, 7.5 Hz, 1H; 3.64, dd, J=10.8, 2.7 Hz, 1H; 3.84, m, 1H; MS (DCI/NH$_3$) m/z 176 (M+NH$_4$)$^+$.

EXAMPLE 15C (S)-cyclohexylmethyloxirane

To a solution of the product from Example 15B in CH$_2$Cl$_2$ was added triethylamine (6.6 mL), 2,4,6-triisopropylbenzenesulfonyl chloride (11.5 g), and DMAP (0.386 g). After 14 hours, the reaction was diluted with ether, chilled to 0° C., filtered through celite, and concentrated. The residue was dissolved in ethanol (100 mL) and 1M NaOH (32 mL) was added. After 30 minutes, the reaction was carefully concentrated, diluted with water (100 mL), and extracted into ether (3×50 mL). The organic extracts were washed with brine (20 mL), dried (MgSO$_4$), filtered, and concentrated to provide a colorless aromatic oil which was purified first by passage through a plug of silica gel eluting with 5% EtOAc/hexanes, then by bulb-to-bulb distillation under reduced pressure to provide 3.3 g (75%) of the title compound as a colorless aromatic oil.
$^1$H NMR (300 MHz, CDCl$_3$) δ 0.90–1.09, m, 2H; 1.10–1.85, m, 11H; 2.43, dd, J=5.1, 2.7 Hz, 1H; 2.75, dd, J=5.1, 4.5 Hz, 1H; 2.94, m, 1H.

EXAMPLE 15D (S)-3-cyclohexyl-1-ethylthiopropan-2-ol

Ethanethiol (317 μL, 4.3 mmol) was added to a 60% dispersion in mineral oil NaH (180 mg, 4.5 mmol) slurry in DMF (26 mL) at ambient temperature. After stirring for 15 minutes, the product from Example 15C (300 mg, 2.1 mmol) in DMF (2.0 mL) was added to the reaction vessel. After stirring for 30 minutes, a solution of saturated NH$_4$Cl was added to the mixture followed by extraction with EtOAc (2×). The organics were combined, dried (MgSO$_4$), and concentrated. The residue was chromatographed (silica gel; EtOAc/hexanes 1:20) to provide 347 mg (80%) of the title compound as a light yellow oil.
$^1$H NMR (300 MHz, CDCl$_3$) δ 0.80–1.00, m, 2H; 1.12–1.32, m, 7H; 1.39–1.75, m, 6H; 1.81, m, 1H; 2.42, dd, J=9, 14 Hz, 1H; 2.56, q, J=7.5 Hz, 2H; 2.74, dd, J=3, 14 Hz, 1H; 3.76, m, 1H; MS (CI/NH$_3$) m/z 203 (M+H)$^+$.

EXAMPLE 15E

N-4-[(N'-2(S)-1-ethylthio-3-cyclohexyl-2-propoxycarbonyl)-3-(2-methylphenyl)-1,2,5,6-tetrahydroisonicotinyl]methionine, methyl ester Following the procedure for Example 1I, the products from Example 1H (150 mg, 0.38 mmol) and Example 15D (85 mg, 0.42 mmol) provided 108 mg (48%) of the title compound.
MS (ESI(+)) m/z 591 (M+H)$^+$, (ESI(−)) 589 (M−H)$^-$.

EXAMPLE 15F

N-4-[(N'-2(S)-1-ethylthio-3-cyclohexyl-2-propoxycarbonyl)-3-(2-methylphenyl)-1,2,5,6-tetrahydroisonicotinyl]methionine lithium salt Following the procedure for Example 20D, the product from Example 15E provided the title compound.
$^1$H NMR (300 MHz, DMSO-$d_6$) δ 7.06–7.24, m, 3H; 6.95, m, 1H; 6.67, m, 1H; 4.89, quintet, 1H; 4.08, m, 1H; 3.40–3.87, m, 4H; 2.69, m, 2H; 2.42–2.60, m, 3H; 2.11–2.37, m, 4H; 1.84, s, 3H; 0.75–1.80, m, 22H; MS (ESI(+)) m/z 577 (M+H)$^+$, (ESI(−)) 575 (M−H)$^-$; Anal. calc'd for $C_{30}H_{43}N_2O_5S_2Li \cdot 1.69\ H_2O$: C, 58.77; H, 7.62; N, 4.57. Found C, 58.76; H, 7.23; N, 4.69.

EXAMPLE 16

N-4-[(N'-2-cyclohexyloxyethoxycarbonyl)-3-(2-methylphenyl)-1,2,5,6-tetrahydroisonicotinyl] methionine, lithium salt

EXAMPLE 16A

N-4-[(N'-2-cyclohexyloxyethoxycarbonyl)-3-(2-methylphenyl)-1,2,5,6-tetrahydroisonicotinyl] methionine, methyl ester Following the procedure for Example 1I, the product from Example 1H (150 mg, 0.38 mmol) and 2-cyclohexyloxyethanol (0.064 mL, 0.44 mmol) provided 111 mg (55%) of the title compound.
MS (ESI(+)) m/z 527 (M+H)$^+$, (ESI(−)) 525 (M−H)$^−$.

EXAMPLE 16B

N-4-[(N'-2-cyclohexyloxyethoxycarbonyl)-3-(2-methylphenyl)-1,2,5,6-tetrahydroisonicotinyl] methionine, lithium salt Following the procedure for Example 20D, the product from Example 16A provided the title compound.
$^1$H NMR (300 MHz, DMSO-d$_6$) δ 7.50, bs, 1H; 7.02–7.28, m, 4H; 3.97–4.22, m, 4H; 3.20–3.90, m, 8H; 2.19, bs, 3H; 1.90, s, 3H; 1.08–1.85, m, 14H; MS (ESI(+)) m/z 513 (M+H)$^+$, (ESI(−)) 511 (M−H)$^−$; Anal. calc'd for C$_{27}$H$_{38}$N$_2$O$_6$S.0.73 H$_2$O: C, 60.98; H, 7.48; N, 5.27. Found: C, 60.98; H, 7.28; N, 5.36.

EXAMPLE 17

N-4-[1-N'-(N"-2-cyclhexylethylmethylaminocarbonyl)-3-(2-methylphenyl)-1,2,5,6-tetrahydroisonicotinyl] methionine

EXAMPLE 17A

N-2-cyclohexylethyl-N-5-thiazolemethylamine

Following the procedure from Example 8A, cyclohexyl-ethylamine and 5-thiazolecarboxaldehyde provided the title compound.
MS (DCI/NH$_3$) m/z 225 (M+H)$^+$.

EXAMPLE 17B

N-4-[1-(N'-cyclohexylethyll-5-thiazolmethylaminocarbonyl)-3-(2-methylphenyl)-1, 2,5,6-tetrahydroisonicotinyl]methionine, methyl ester Following the procedure for Example 3B, the products from Example 1H (199 mg, 0.50 mmol) and Example 17A (123 mg, 0.55 mmol) provided 117 mg (38%) of the title compound.
MS (ESI(+)) mn/z 613 (M+H)$^+$, (ESI(−)) 611 (M−H)$^−$.

EXAMPLE 17C

N-4-[1-N'-(N"-2-cyclhexylethylmethylaminocarbonyl)-3-(2-methylphenyl)-1,2,5,6-tetrahydroisonicotinyl] methionine Following the procedure for Example 1J, the product from Example 17B was converted to the title compound.
$^1$H NMR (300 MHz, DMSO-d$_6$) δ 9.02, s, 1H; 8.84, s, 1H; 7.30–7.52, m, 1H; 6.95–7.19, m, 4H; 5.52, d, 2H; 4.08, m, 1H; 3.84, d, 1H; 3.72, d, 1H; 3.47, m, 2H; 3.03, m, 2H; 2.10–2.63, m, 1.88, s, 3H; 1.49–1.76, m, 8H; 1.41, q, 2H; 1.12, m, 4H; 0.85, m, 2H; MS (ESI(+)) ni/z 599 (M+H)$^+$, 621 (M+Na)$^−$, (ESI(−)) 597 (M−H)$^−$; Anal. calc'd for C$_3$IH$_{40}$N$_4$O$_4$S$_2$: C, 62.18; H, 7.07; N, 9.36. Found: C, 61.82; H, 6.90; N, 9.08.

EXAMPLE 18

N-4-[1-(4-phenoxybutyl)-3-(2-methylphenyl)-1,2,5, 6-tetrahydroisonicotinyl]methionine

EXAMPLE 18A

N-4-[1-(4-phenoxbutyl)-3-(2-methylphenyl)-1,2,5,6-tetrahydroisonicotinyl]methionine, methyl ester A solution of the product from Example 1H (200 mg, 0.5 mmol), 4-phenoxybutyl bromide (126 mg, 0.55 mmol), tetrabutylammonium iodide (203 mg, 0.55 mmol), and Hunigs' base (0.21 mL, 1.2 mmol) in 3 mL of acetonitrile was heated to 50° C. for 24 hours. After the reaction had cooled to room temperature, the mixture was poured into water and extracted with 3 portions of ethyl acetate. The combined organic phases were washed with water and brine, dried (Na$_2$SO$_4$), filtered, and concentrated. The residue was purified by column chromatography on silica gel (20 g, ethyl acetate) to provide 137 mg (54%) of the title compound.
MS (ESI(+)) m/z 51 1 (M+H)$^+$, (ESI(−)) 509 (M−H)$^−$.

EXAMPLE 18B

N-4-[1-(4-phenoxybutyl)-3-(2-methylphenyl)-1,2,5, 6-tetrahydroisonicotinyl]methionine Following the procedure for Example 1J, the product from Example 18A was converted to the title compound.
$^1$H NMR (300 MHz, DMSO-d$_6$) δ 7.28, m, 3H; 7.05–7.23, m, 4H; 6.91, m, 3H; 4.07, m, 1H; 3.98, t, 2H; 2.57, m, 2H; 2.63, m, 1H; 2.79, m, 1H; 2.95, bd, 1H; 3.16, d, 1H; 2.29 . 2.50, m 2H; 1.28, bs, 3H; 1.89, s, 3H; 1.41–1.86, m, 8H; MS (ESI(+)) m/z 497 (M+H)$^+$, 519 (M+Na)$^−$, (ESI(−)) 495 (M−H)$^−$; Anal. calc'd for C$_{28}$H$_{36}$N$_2$O$_4$S.0.79 H$_2$O: C, 65.83; H, 7.41; N, 5.48. Found: C, 65.84; H, 7.45; N, 5.26.

EXAMPLE 19

N-4-[1-(2-[R*,S*]-benzyloxyhexyl)-3-(2-methylphenyl)-1,2,5,6-tetrahydroisonicotinyl] methionine, lithium salt

EXAMPLE 19A 5-n-butyl-2-phenyl-1,3-dioxolane

A solution of benzaldehyde (5.1 mL, 50.0 mmol), 1,2-hexanediol (6.5 g, 55.0 mmol), and camphorsulfonic acid (0.58 g, 2.5 mmol) in 50 mL of toluene was heated to reflux (Dean-Stark) with azeotropic removal of water. When the theoretical amount of water was distilled (4.5 hours), the mixture was cooled to room temperature and diluted with 80 mL of ether. The solution was extracted with 2M aqueous sodium carbonate, water and brine, dried (Na$_2$SO$_4$), filtered, and concentrated to provide 10.54 g (102%) of the title compound.
MS (DCI/NH$_3$) m/z 207 (M+H)$^+$, 224 (M+NH$_4$)+.

EXAMPLE 19B

2(R,S)-benzyl-1,2-hexanediol

A solution of the product from Example 19A (2.06 g, 10.00 mmol) in 10 mL of toluene was cooled in an ice bath and treated with diisobutylalumium hydride (16.6 mL of a 1.5M toluene solution, 25 mmol). The mixture was stirred for 15 minutes at 0° C. and 1 hour at room temperature and carefully quenched by the dropwise addition of 10% methanol/toluene (vigorous gas evolution). After stirring for 1 hour at ambient temperature, the cloudy mixture was treated with 50 mL of 3N aqueous hydrochloric acid and vigorously stirred until 2 clear phases resulted. The phases were separated and the aqueous phase was extracted with 2 portions of ethyl ether. The combined organic phases were washed with 2 portions of water and 2 portions of brine, dried (Na$_2$SO$_4$), filtered, and concentrated. The residue was purified by column chromatography on silica gel (20% ethyl acetate/hexanes) eluting the 1-benzyl isomer (0.17 g, 8%) first, followed by 1.50 g (72%) of the title compound.

MS (DCI/NLI-1$_3$) m/z 209 (M+H)$^+$, 226 (M+NH$_4$)$^+$.

EXAMPLE 19C 1-methanesulfonyl-2(R,S)-benzyl-1,2-hexanediol

To a stirred solution of the product from Example 19B (416 mg, 2.0 mmol) in 4 mL of dichloromethane at 0° C. was added triethylamine (0.34 mL, 2.4 mmol) followed by the addition of methanesulfonyl chloride (0.17 mL, 2.2 mmol). The mixture was placed in a refrigerator overnight. The resulting cloudy mixture was diluted with ethyl acetate and extracted with water, 3N aqueous HCl, water and brine, dried (Na$_2$SO$_4$), filtered, and concentrated to provide 552 mg (96%) of the title compound as an oil that was used directly.

EXAMPLE 19D

N-4-[1-(2-[R*,S*]-benyloxyhexyl)-3-(2-methylphenyl)-1,2,5,6-tetrahydroisonicotinyl] methionine, methyl ester A solution of the product from Example 19C (172 mg, 0.6 mmol), the product from Example 1H (200 mg, 0.5 mmol), tetrabutylammonium iodide (222 mg, 0.6 mmol), and Hunigs' base (0.20 mL, 1.10 mmol) in 2 mL of acetonitrile was heated to 45° C. for 8 hours. The temperature was raised to 60° C. and heating continued for 48 hours. The mixture was cooled to room temperature and diluted with aqueous NaHCO$_3$. The aqueous mixture was extracted with 3 portions of ethyl acetate and the combined organic extracts were washed with brine, dried (Na$_2$SO$_4$), filtered, and concentrated. The residue was purified by column chromatography (silica gel) eluting with 50% ethyl acetate/hexanes to provide 51 mg (18%) of the title compound.
MS (ESI(+)) rn/z 553 (M+H)$^+$, (ESI(-)) 551 (M-H)$^-$.

EXAMPLE 19E

N-4-[1-(2-[R*,S*]-benzyloxyhexvl)-3-(2-methylphenyl)-1,2,5,6-tetrahydroisonicotinyl] methionine lithium salt A solution of the product from Example 19D (49 mg, 0.09 mmol) in 1:1 methanol/THF was treated with 1M aqueous lithium hydroxide (0.18 mL, 0.18 mmol) and the resulting solution stirred at ambient temperature overnight. The solution was concentrated to dryness and lyophilized to provide the title compound as a 1:1 complex with lithium hydroxide.
$^1$H NMR (300 MHz, DMSO-d$_6$) δ 7.30, m, 5H; 7.13, m, 4H; 6.57, d, 1H; 4.55, q, 2H; 3.57, m, 2H; 3.13–3.38, m, 2H; 2.83, m, 2H; 2.41–2.63, m, 2H; 2.09–2.35, m, 5H; 1.85, s, 3H; 1.70, m, 1H; 1.20–1.64, m, 10H; 0.86, t, 3H; MS (ESI(+)) m/z 539 (M+H)$^+$, 561 (M+Na)$^-$, (ESI(-)) 537 (M-H)$^-$; Anal. calc'd for C$_{31}$H$_{42}$N$_2$O$_5$SLi$_2$.1.05 H$_2$O: C, 63.37; H, 7.57; N, 4.77. Found C, 63.37; H, 7.19; N, 4.64.

EXAMPLE 20

N-4-[1-(2-[R*,S*]-cyclohexylmethyloxyhexyl)-3-(2-methylphenyl)-1,2,5,6-tetrahydroisonicotinyl] methionine, lithium salt

EXAMPLE 20A

2(R,S)-cyclohexylmethyl-1,2-hexanediol

A solution of the product from Example 19B (1.07 g, 5.19 mmol) was reduced using hydrogen gas at 4 atm in the presence of Rh/alumina in methanol to provide 1.02 g (92%) of the title compound.
MS (DCI/NH$_3$) m/z 215 (M+H)$^-$; 232 (M+NH$_4$)$^+$.

EXAMPLE 20B 1-4-methylphenylsulfonyl-2-cyclohexylmethyl-1,2-hexanediol

A solution of the product from Example 20A (214 mg, 1.00 mmol) in 1 mL of pyridine at 0° C. was treated with toluenesulfonyl chloride (210 mg, 1.10 mmol). The mixture was placed in a refrigerator overnight and stirred at room temperature for 4 hours. The solution was diluted with ether and extracted with water, 1M aqueous phophoric acid, 2M aqueous sodium carbonate, and brine, dried (Na$_2$SO$_4$), filtered, and concentrated to provide the title compound that was used directly.

EXAMPLE 20C

N-4-[1-(2-[R*,S*]-cyclohexylmethyloxyhexyl)-3-(2-methylphenyl)-1,2,5,6-tetrahydroisonicotinyl] methionine, methyl ester Following the procedure for Example 19D, the products from Example 1H (336 mg, 0.84 mmol) and Example 20B (310 mg, 0.84 mmol) were combined to provide 94 mg (20%) of the title compound.
MS (ESI(+)) m/z 559 (M+H)$^+$, (ESI(-)) 557 (M-H)$^-$.

EXAMPLE 20D

N-4-[1-(2-[R*,S*]-cyclohexylmethyloxyhexy)-3-(2-methylphenyl)-1,2,5,6-tetrahydroisonicotinyl] methionine, lithium salt Following the procedure for Example 1J, the product from Example 20C was converted to the free acid of the title compound. The acid was treated with 1 equivalent of aqueous lithium hydroxide and lyophilized to provide the title compound as the lithium carboxylate.
$^1$H NMR (300 MHz, CD$_3$OD) δ 7.10–7.25, m, 4H; 7.03, d, 1H; 4.13, m, 1H; 4.08, m, 1H; 3.52, m, 2H; 3.41, m, 1H; 3.23–3.35, m, 3H; 2.96, m, 2H; 2.63–2.90, m, 4H; 2.22–2.44, m, 3H; 1.93, m, 4H; 1.12–1.85, m, 13H; 0.92, m, 5H; MS (ESI(+)) m/z 545 (M+H)$^+$, (ESI(-)) 543 (M-H)$^-$; Anal. calc'd for C$_{31}$H$_{47}$N$_2$O$_4$SLi.0.95 H$_2$O: C, 65.57; H, 8.68; N, 4.93. Found: C, 65.69; H, 8.68; N, 4.77.

EXAMPLE 21

N-4-[1-(2-[R*,S*]-5-(1-hydroxy-3-cyclohexvlpropyl)thiazolyloxycarbonyl)-3-(2-methylphenyl)-1,2,5,6-tetrahydroisonicotinyl] methionine, lithium salt

EXAMPLE 21 A

5-[1-(R*,S*)-hydroxy-3-cyclohexylpropyl]thiazole

To a solution of 2-cyclohexylethylmagnesium bromide (40.8 mmol, prepared from the corresponding bromide and magnesium turnings) in 40 mL of ethyl ether at 0° C. was added dropwise, a solution of 5-thiazolecarboxaldehyde (2.31 g, 20.40 mmol) in 20 mL of THF. After completion of the addition, the cooling bath was removed and the mixture was stirred at room temperature for 2 hours. The reaction was quenched by the careful addition of 3N aqueous HCl and the mixture stirred vigorously until 2 clear phases resulted. The ether layer was removed and the pH of the aqueous phase adjusted to ca.4 by the addition of aqueous 2M sodium carbonate and extracted with 2 portions of ethyl acetate. The combined organic fractions were washed with brine, dried ($Na_2SO_4$), filtered, and concentrated. The residue was purified by column chromatography (silica gel, 50% ethyl acetate/hexanes) to provide 2.69 g (58%) of the title compound.

MS ($DCI/NH_3$) m/z 226 $(M+H)^+$, 243 $(M+NH_4)+$.

EXAMPLE 21B

N-4-[1-(2-[R*,S*]-5-(1-hydroxy-3-cyclohexylipropyl)thiazolyloxycarbonyl)-3-(2-methylphenyl)-1,2,5,6-tetrahydroisonicotinyl] methionine, methyl ester Following the procedure for Example 11, the product from Example 21A (270 mg, 1.2 mmol) and the product from Example 1H (399 mg, 1.00 mmol) were converted to (205 mg, 33%) the title compound.

MS (ESI(+)) m/z 614 $(M+H)^+$, (ESI(−)) 612 $(M-H)^-$.

EXAMPLE 21C

N-4-[1-(2-[R*,S*]-5-(1-hydroxy-3-cyclohexylpropyl)thiazolyloxycarbonyl)-3-(2-methylphenyl)-1,2,5,6-tetrahydroisonicotinyl] methionine, lithium salt Following the procedure for Example 20D, the product from Example 21B was converted to the title compound.

$^1$H NMR (300 MHz, DMSO-$d_6$) δ 9.07, s, 1H; 7.90, s, 1H; 7.17, m, 4H; 6.64, bs, 1H; 5.95, t, 1H; 4.06, m, 1H; 3.75, m, 2H; 3.50, m, 2H; 2.48–2.65, m, 2H; 1.90–2.43, m, 6H; 1.87, s, 3H; 1.50–1.75, m, 6H; 1.43, m, 2H; 1.00–1.34, m, 6H; 0.85, m, 2H; MS (ESI(+)) m/z 600 $(M+H)^+$, 622 $(M+Na)^-$, (ESI(−)) 598 $(M-H)^-$; Anal. calc'd for $C_{31}H_{40}N_3O_5S_2Li$.2.15 $H_2O$: C, 57.77; H, 6.93; N, 6.52. Found: C, 57.79; H, 6.50; N, 6.24.

EXAMPLE 22

N-4-[1-(4-methyl-[R*,S*]-5-(1-hydroxy-2-cyclohexylethyl)thiazolyloxycarbonyl)-3-(2-methylphenyl)-1,2,5,6-tetrahydroisonicotinyl] methionine, methyl ester

EXAMPLE 22A ethyl 2-amino-4-methylthiazole-5-carboxylate

A 50 mL round-bottom flask was charged with ethyl acetoacetate (6.4 mL, 50 mmol) and water (25 mL). Bromine (2.8 mL, 51 mmol) was added over 30 minutes and an orange solution formed. The reaction was added to diethyl ether (100 mL). The organic layer was dried ($MgSO_4$) and solvent removed under vacuum. The remaining orange gel was added to a refluxing solution of thiourea (8.95 g, 117.5 mL) in ethanol (25 mL). The reaction was refluxed for approximately 2 hours, cooled slightly, and poured into 50 mL of ice water. The pH was adjusted to ca.7–9 with $NH_4OH$. A thick white precipitate formed. The mixture was filtered to collect the solid. The product was recrystallized from 95% EtOH to provide 7.3 g (78%) of the title compound as a white, fluffy crystalline solid.

$^1$H NMR (300 MHz, $CDCl_3$) δ 4.6, q, 3H; 2.55, s, 3H; 1.35, t, 2H; MS ($DCI/NH_3$) m/z 187 $(M+H)^+$.

EXAMPLE 22B ethyl 4-methylthiazole-5-carboxylate

A 50 mL round-bottom flask was charged with 4N $H_2SO_4$ (80 mL) and the product from Example 22A (2.23 g, 12 mmol). The reaction was cooled to −5° C. Sodium nitrite (0.99 g, 14.4 mmol), in 5 mL $H_2O$, was added over 5 minutes. The reaction was stirred for approximately 30 minutes, then slowly treated with 50% (by wt) $H_3PO_2$ (15.84 mL, 120 mmol). A thick orange foam formed. The reaction was allowed to stir for approximately 3 hours until the foam subsided and 50 mL of water was added. The pH was adjusted to approximately 4–5 with potassium phosphate. The reaction was extracted with $Et_2O$ (3×50 mL), dried ($Na_2SO_4$), and concentrated under vacuum. The residue was purified by column chromatography on silica gel (3: 1 hexanes/EtOAc) to provide 1.50 g (67% ) of the title compound as an orange oil.

$^1$H NMR (300 MHz, $CDCl_3$) δ 7.7, s, 1H; 4.35, q, 3H; 2.78, s, 3H; 1.39, t, 2H; MS ($DCI/NH_3$) m/z 172 $(M+H)^+$.

EXAMPLE 22C 2-hydroxymethyl-4-methyl-thiazole

A 50 mL round-bottom flask, under $N_2$ purge, was charged with the product from Example 22B (1.28 g, 7.5 mmol) and ethanol (15 mL). Calcium chloride (1.66 g, 15 mmol) was added and stirred until all the solid had dissolved. Sodium borohydride (1.14 g, 30 mmol) and THF (8 mL) were added. The reaction was stirred at room temperature for approximately 48 hours. The reaction mixture was quenched with 2 mL water. Saturated $NaHCO_3$ was added forming a white precipitate. The mixture was extracted with $Et_2O$ (3×10 mL) and then EtOAc (3×5 mL). The aqueous layer was stirred overnight with 2M $Na_2CO_3$ (25 mL) and combined with the organic layers. The solution was extracted with methylene chloride (3×25 mL) and washed with brine, dried ($MgSO_4$), and concentrated under vacuum to provide 663.4 mg (68%) of the title compound as a pale yellow solid.

$^1$H NMR (300 MHz, $CDCl_3$) δ 8.7, s, 1H; 4.84, s, 2H; 2.45, s, 3H.

EXAMPLE 22D 4-methylthiazole-5-carboxaldehyde

A 3-neck, 100 mL round-bottom flask was charged with anhydrous $CH_2Cl_2$ (15 mL) and oxalyl chloride (0.54 mL, 6.24 mmol) under $N_2$ atmosphere. The mixture was cooled to −78° C. Anhydrous DMSO (0.59 mL, 8.32 mmol) was slowly added. The reaction was allowed to stir for 30 minutes. The product from Example 22C (537.5 mg, 4.16 mmol) in $CH_2Cl_2$ (5 mL) was slowly added. The reaction was allowed to stir for approximately 3 hours, until TLC (1:1 EtOAc/hexanes) showed no starting material. The reaction was quenched with triethylamine (2.4 mL, 16.64 mmol) and stirred for 10 minutes before warming to room temperature. The reaction was poured into $Et_2O$ (100 mL) and extracted with water (2×25 mL). The organic phase was washed with $NaHCO_3$ (25 mL) and brine. The organic phase was dried ($MgSO_4$) and concentrated under vacuum. The crude product was stored in the freezer to provide 461.0 mg (87%) of the title compound as an orange crystalline solid.

$^1$H NMR (300 MHz, $CDCl_3$) δ 10.15, s, 1H; 8.9, s, 1H; 2.8, s, 3H.

EXAMPLE 22E 4-methyl-5-(1-hydroxy-2-cyclohexylethyl)thiazole

A 3-neck, 100 mL round-bottom flask was charged with the product from Example 22D (412.6 mg, 3.5 mmol) and anhydrous THF (15 mL) under $N_2$ atmosphere. The reaction was cooled to −10° C. Cyclohexylmethylmagnesium bromide (7 mL, of a 1.0M solution in ether, 7 mmol) was added dropwise. The reaction was stirred for 1 hour, warmed to room temperature, and stirred for an additional 3 hours. The reaction was quenched with 10 mL THF/1M HCl (1:1). The aqueous and organic layers were separated. The pH of the aqueous layer was adjusted to 3 with 1M HCl. The aqueous layer was extracted with EtOAc (3×10 mL). All organic layers were combined and washed with brine, dried ($MgSO_4$), and concentrated under vacuum. The residue was purified by silica gel column (1:1 EtOAc/hexanes) to provide 425.2 mg (58%) of the title compound as an orange oil.

$^1$H NMR (300 MHz, $CDCl_3$) δ 8.64, s, 1H; 5.15, dd, 2H; 2.44, s, 3H; 2.0–0.9, m, 10H.

EXAMPLE 22F

N-4-[1-(4-methyl-[R*,S*]-5-(1-hydroxy-2-cyclohexylethyl)thiazolyloxycarbonyl)-3-(2-methylphenyl)-1,2,5,6-tetrahydroisonicotinyl] methionine, methyl ester Following the procedure for Example 1I, the product from Example 22E and the product from Example 1H were converted to the title compound.

MS (ESI(+)) m/z 614 (M+H)$^+$, (ESI(−)) 612 (M−H)$^-$.

EXAMPLE 22G

N-4-[1-(4-methl-[R*,S*]-5-(1-hydroxy-2-cyclohexylcthyl)thiazolyloxycarbonyl)-3-(2-methylphenyl)-1,2,5,6-tetrahydroisonicotinyl] methionine, methyl ester Following the procedure for Example 20D, the product from Example 22F was converted to the title compound.

$^1$H NMR (300 MHz, $CDCl_3$) δ 8.65, s, 1H; 6.0–7.3, m, ar; 3.4–4.2, m; 2.55, s, 3H; 0.8–2.5, m; MS (ESI(+)) m/z 600, (ESI(−)) 598;

EXAMPLE 23

N-[4-(2',2'-biscyclohexylmethyl-2'-aminoethyl)-3-(2-methylphenyl)-1,2,5,6-tetrahydroisonicotinyl] methionine, lithium salt

EXAMPLE 23A

N-2'-phthalimidoethyl-3-(2-methylphenyl)-1,2,5,6-tetrahydroisonicotine methyl ester A 100 mL 3-neck, round-bottom flask, fitted with a condenser, was charged with the product from Example 1E (2.011 g, 7.5 mmol), N-(2-bromoethyl)phthalimide (2.097 g, 8.25 mmol), N,N-diisopropylethylamine (3 mL, 16.5 mmol), tetrabutylammonium iodide (3.047 g, 8.25 mmol) and anhydrous DMF (7.5 mL) under $N_2$ purge. The reaction was heated to 100° C. in an oil bath for 24 hours. TLC (1:1 EtOAc/hexanes) showed no starting material. The bath was removed and the reaction cooled slightly. The solution was poured into water (30 mL) and extracted with EtOAc (3×20 mL). The combined organic layers were washed with water (10 mL) and brine, dried ($Na_2SO_4$), and concentrated under vacuum. The product was purified by silica gel column (1:1 EtOAc/hexanes) to provide 2.21 g (73%) of the title compound as an orange sticky solid.

$^1$H NMR (300 MHz, $CDCl_3$) δ 7.8 (ddd, 4H), 6.8–7.2 (m, 4H), 3,85 (t, 2H), 3,4 (s, 2H), 3.2 (br. s, 2H), 2.75 (t, 4H), 2.5 (br.s, 2H), 2,15 (s, 3H).

EXAMPLE 23B

N-2'-aminoethyl-3-(2-methylphenyl)-1,2,5,6-tetrahydroisonicotine methyl ester complex with phthalhydrazide A 100 mL round-bottom flask, under $N_2$ purge was charged with the product from Example 23A (2.207 g, 5.46 mmol). Ilydrazine (0.2 mL, 5.46 mmol) dissolved in methanol (30 mL) was added slowly via addition funnel. The flask was warmed with a warm water bath to dissolve the starting material. The reaction was stirred for 24 hours forming a pale yellow slurry. The solvent was removed under vacuum. The solid was dissolved in 10 mL ethanol and reconcentrated under vacuum. The procedure was repeated twice more and dried under high vacuum to provide 3.15 g of the title compound an an orange-white solid.

MS (ESI(+)) m/z 437 (M+H)$^+$, (ESI(−)) 435 (M−H)$^-$.

EXAMPLE 23C

N-[N'-1',1'-dimethylethoxycarbonyl-2'-aminoethyl]-3-(2-methylphenyl)-1,2,5,6-tetrahydroisonicotine A 100 mL round-bottom flask, fitted with a condenser, was charged with the product from Example 23B (3.150 g, 7.22 mmol), 4N sodium hydroxide (14.6 mL, 57.76 mmol), and ethanol (35 mL). The reaction was refluxed for 2 hours and cooled. The solvent was removed under vacuum. The product was redissolved in THF (15 mL) and water (10 mL). Di-tert-butyldicarbonate (2.364 g, 10.83 mmol) was added. The reaction was stirred for 12 hours at room temperature and extracted with $Et_2O$ (2×25 mL). The combined organic phases were washed with 1M NaOH (25 mL) and water (25 mL). The resulting aqueous phases were combined, the pH was adjusted to 6 with 1M $H_3PO_4$, and extracted with EtOAc (3×25 mL). The resulting organic phases were combined, washed with brine, dried ($Na_2SO_4$), and concentrated to provide 1.05 g (50%) of the title compound as an orange solid.

MS (ESI(−)) m/z 359 (M−H)$^-$.

EXAMPLE 23D

N-[4-(1',1'-dimethylethoxycarbonyl-2'-aminoethyl)-3-(2-methylphenyl)-1,2,5,6-tetrahydroisonicotinyl] methionine, methyl ester A 100 mL round-bottom flask was charged with the product from Example 23C (1.044 g, 2.91 mmol), EDC (611.8 mg, 3.19 mmol), L-methionine methyl ester hydrochloride (757.3 mg, 3.79 mmol), HOBt (432.5 mg, 3.19 mmol), and DMF (6 mL). The reagents were stirred until completely dissolved and triethylamine (0.75 mL, 5.22 mmol) was added. The reaction was stirred for 72 hours at room temperature until TLC (1:1 EtOAc/hexanes ) showed no reaction. Another equivalent of each reagent was added and heated at 50° C. for 12 hours. The reaction was cooled and the pH adjusted to 9 with saturated $NaHCO_3$. The solution was extracted with EtOAc (4×10 mL), washed with 2M $Na_2CO_3$ (20 mL), water (20 mL), and brine, dried ($Na_2SO_4$) and concentrated. The product was purified by silica gel column (80% EtOAc/hexanes) to provide 649.3 mg (44%) of the title compound as a yellow solid.

MS (ESI(+)) m/z 506 (M+H)$^+$, (ESI(−)) 504 (M−H)$^-$.

EXAMPLE 23E

N-[4-(2'-aminoethyl)-3-(2-methylphenyl)-1,2,5,6-tetrahydroisonicotinyl]methionine, methyl ester, hydrochloride salt A 25 mL round-bottom flask was charged with the product from Example 23D (649.3 mg, 1.29 mmol) and 4M HCl in dioxane (2 mL). The reaction was stirred for 90 minutes and concentrated under vacuum to provide 517.0 mg (91%) of the title compound as an orange-brown solid.
MS (ESI(+)) m/z 406 (M+H)$^+$, (ESI(−)) 404 (M−H)$^-$.

EXAMPLE 23F

N-[4-(2',2'-biscyclohexylmethyl-2'-aminoethyl)-3-(2-methylphenyl)-1,2,5,6-tetrahydroisonicotinyl] methionine, methyl ester A 25 mL round-bottom flask was charged with the product from Example 23E (110.7 mg, 0.25 mmol) and 1,2-dichloroethane (3 mL) under $N_2$ atmosphere. N,N-diisopropylamine (0.1 mL, 0.275 mmol) was added via syringe. Cyclohexanecarboxaldehyde (0.04 mL, 0.275 mmol) and glacial acetic acid (0.06 mL, 1.0 mmol) were also added via syringe. The reaction was stirred for 6 hours and sodium triacetoxyborohydride (160.2 mg, 0.75 mmol) was added. The reaction was stirred for an additional 12 hours. The mixture was diluted with water, extracted with $CH_2Cl_2$ (3×10 mL), dried ($Na_2SO_4$), and concentrated to provide 158.7 mg of the title compound as an orange oil.
MS (ESI(+)) m/z 598 (M+H)$^+$, (ESI(−)) 596 (M−H)$^-$.

EXAMPLE 23G

N-[4-(2', 2'-biscyclohexylmethyl-2'-aminoethyl)-3-(2-methylphenyl)-1,2,5,6-tetrahydroisonicotinyl] methionine, Following the procedure for Example 1J, the product from Example 23F was converted into the title compound (69.9 mg, 45%) as an orange solid.
MS (ESI(+)) m/z 584 (M+H)$^+$, (ESI(−)) m/z 582 (M−H)$^-$.

EXAMPLE 23H

N-[4-(2', 2'-biscyclohexylmethyl-2'-aminoethyl)-3-(2-methylphenyl)-1,2,5,6-tetrahydroisonicotinyl] methionine, lithium salt Following the procedure for Example 20D, the product from Example 23G was converted into the title compound 30.0 mg as an orange solid.
$^1$H NMR (300 MHz, DMSO-$d_6$) δ 6.5–7.2 (envelope, 4H), 5.7 (s, 1H), 3.5 (br.s, I H), 2.5–3.2 (envelope, 4H), 1.9–2.45 (envelope, 12H), 1.85 (s, 3H), 1.65 (br.m, 8H), 1.6 (s, 3H), 1.35 (envelope, 4H), 1.15 (m, 8H), 0.8 (m, 4H); MS (ESI(+)) m/z 584 (M+H)$^+$, (ESI(−))582 (M−H)$^-$; Anal. calc'd for $C_{34}H_{52}LiN_3O_3S.3.90$ 120: C, 61.87; H, 9.13; N, 6.37. Found: C, 61.77; H, 8.40; N, 6.96.

EXAMPLE 24

N-[4-(2', 2'-bis(5-thiazolemethyl)-2'-aminoethyl)-3-(2-methylphenyl)-1,2,5,6-tetrahydroisonicotinyl] methionine. lithium salt

EXAMPLE 24A

N-2'-aminoethyl-3-(2-methylphenyl)-1,2,5,6-tetrahydroisonicotine methyl ester dihydrochloride salt A 100 mL round-bottom flask was charged with the product from Example 23B (2.062 g, 4.73 mmol) and THF (50 mL). A cream-colored slurry formed. The reaction was cooled in an ice bath and concentrated HCl (1 mL) was added. The reaction was stirred for a few minutes and allowed to warm to room temperature. The liquid was decanted and the grey solid was washed twice with hot THF and dried ($Na_2SO_4$) under vacuum to provide 2.46 g of the title compound as a pale yellow powder.
MS (DCI/$NH_3$) m/z 275 (M+H)$^+$.

EXAMPLE 24B 1-(2',2'-bis)5-thiazolemethyl)-2'-aminoethyl)-3-(2-methylphenyl)-1,2,5,6-tetrahydroisonicotine methyl ester A 50 mL round-bottom flask was charged with the product from Example 24A (500.9 mg, 1.44 mmol) and 1,2-dichloroethane (5 mL) under $N_2$ purge. Sodium sulfate was added along with 2-thiazolecarboxaldehyde (0.145 mL, 1.65 mmol), 2 drops of glacial acetic acid, and diisopropylethylamine (0.56 mL, 3.17 mmol). The reaction was stirred for 90 minutes and sodium triacetoxyborohydride (917.6 mg, 4.32 mmol) and acetic acid (0.41 mL, 7.2 mmol) were added. After being stirred for an additional 12 hours, 2M $Na_2CO_3$ (5 mL) was added and stirred for an addtional hour. The reaction mixture was extracted with $CH_2Cl_2$ (4×10 mL), dried ($Na_2SO_4$), and concentrated. The product was purified by silica gel column (3% MeOH, 1% $NH_4OH$/EtOAc) to provide 539.1 mg (80%) of the title compound as a yellow oil.
MS (DCI/$NH_3$) m/z 469 (M+H)$^+$.

EXAMPLE 24C

N-(N',N"-bis(5-thiazolemethyl)-2'-aminoethyl)-3-(2-methylphenyl)-1,2,5,6-tetrahydroisonicotine A 50 mL round-bottom flask was charged with the product from Example 24B (539.1 mg, 1.15 mmol) and ethanol (10 mL). 4N Sodium hydroxide (2.3 ml, 9.20 mmol) was added and the reaction heated to reflux for 1 hour. After cooling, the solvent was removed under vacuum and diluted with water. The solution was extracted with $Et_2O$ (2×10 mL). The aqueous phase was acidified to pH5 with 0.5M $H_3PO_4$ and extracted with EtOAc (3×10 mL). The combined organic layers were dried ($Na_2SO_4$) and concentrated to provide 82.5 mg (16%) of the title compound as a red sticky solid.
MS (DCI/$NH_3$) m/z 455 (M+H)$^+$.

EXAMPLE 24D

N-[4-(2',2'-bis(5-thiazolemethyl)-2'-aminoethyl)-3-(2-methylphenyl)-1,2,5,6-tetrahydroisonicotinyl] methionine, methyl ester Following the procedure for Example 1G, the product from Example 24C was converted into the title compound (51.6 mg, 48%) as an orange sticky solid.
MS (ESI) m/z 600 (M+H)$^+$, (ESI(−)) 598 (M−H)$^-$.

EXAMPLE 24E

N-[4-(2',2'-bis(5-thiazolemethyl)-2'-aminoethyl)-3-(2-methylphenyl)-1,2,5,6-tetrahydroisonicotinyl] methionine, lithium salt Following the procedure for Example 20D, the product from Example 24D was converted into the title compound (42.9 mg, 90%) as an orange solid.
$^1$H NMR (300 MHz, DMSO-$d_6$) δ 7.7 (dd, 411), 6.8–7.2 (envelope, 4H), 6.55 (d, 1H), 5.2 (s, 1H), 4.8 (s, 1H), 4.1 (s, 2H), 3.0–3.6 (envelope, 4H), 2.55–3.0 (envelope, 4H), 1.9–2.5 (envelope, 5H), 1.85 (2, 3H), 1.6 (s, 3H), 1.2–1.55 (envelope 2H); MS (ESI) m/z 586 (M+H)$^+$, 584 (M−H)$^-$.

EXAMPLE 25

N-[4-(2',2'-di-butyl-2'-aminoethyl)-3-(2-methylphenyl)-1,2,5,6-tetrahydroisonicotinyl] methionine, lithium salt

EXAMPLE 25A

N-(N',N''-dibutyl-2'-aminoethyl)-3-(2-methylphenyl)-1,2,5,6-tetrahydroisonicotine methyl ester Following the procedure for Example 24B, except 5 equivalents of butryraldehyde was used, the product from Example 24A was converted to 252.8 mg of the title compound as a red oil.
MS (DCI/NH$_3$) m/z 387 (M+H)$^+$.

EXAMPLE 25B

N-(N',N''-dibutyl-2'-aminoethyl)-3-(2-methylphenyl)-1,2,5,6-tetrahydroisonicotine A 50 mL round bottom flask was charged with the product from Example 25A (252.8 mg, 0.65 mmol) and ethanol (10 mL). 4 N Sodium hydroxide (1.3 ml, 5.20 mmol) was added and the reaction heated to reflux for 1 hour. After cooling, the solvent was removed under vacuum and diluted with water and the pH adjusted to 5 with 0.5M H$_3$PO$_4$. The solution was extracted with 5% isopropanol/CHCl$_3$. The combined organic layers were dried over Na$_2$SO$_4$ and concentrated to provide (185.0 mg, 82%) of the title compound as an orange oil.
MS (DCI/NH$_3$) m/z 373 (M+H)$^+$.

EXAMPLE 25C

N-[4-(2',2'-di-butyl-2'-aminoethyl)-3-(2-methylphenyl)-1,2,5,6-tetrahydroisonicotinyl] methionine, methyl ester Following the procedure of Example 1G, the product from Example 25B (185.0 mg, 0.5 mmol) was converted to the title compound (95.7 mg, 37%).
MS (ESI(+)) m/z 518 (M+H)$^+$, (ESI(−))516 (M−H)$^-$.

EXAMPLE 25D

N-[4-(2',2'-di-butyl-2'-aminoethyl)-3-(2-methylphenyl)-1,2,5,6-tetrahydroisonicotinyl] methionine, lithium salt Following the procedure for Example 20D, the product from Example 25C was converted to the title compound (90.8 mg) as a pale yellow solid.
$^1$H NMR (300 MHz, DMSO-d$_6$) δ 6.8–7.2 (envelope, 4H), 6.55 (s, 1H), 3.5 (s, 2H), 3.15 (d, 2H), 2.8 (br.s, 4H), 2.35 (t, 6H), 2.15 (s, 3H), 1.85 (s, 3H), 1.2–1.6 (envelope 12H), 0.85 (t, 3H); MS (ESI) m/z 504 (M+H)$^+$, 502 (M−H)$^-$; Anal. calc'd for C$_{28}$H$_{44}$LiN$_3$O$_3$S.7.0 H$_2$O: C, 52.90; H, 9.20; N, 6.61. Found: C, 52.89; H, 7.55; N, 6.11.

EXAMPLE 26

N-[4-(2',2'-di-butyl-2'-aminoethyl)-3-(2-methylphenyl)-1,2,5,6-tetrahydroisonicotinyl] methionine

EXAMPLE 26A

N-2'-bromoethyl-3-(2-methylphenyl)-1,2,5,6-tetrahydroisonicotine methyl ester

The product from Example 1E (1.250 g) was partitioned between saturated Na$_2$CO$_3$ and CH$_2$Cl$_2$, the organic phase dried (Na$_2$SO$_4$), and concentrated under vacuum to provide the free amine which was used directly. A 50 mL round-bottom flask was charged with the free amine, 1,2-dibromoethane (12.5 mL), N,N-diisopropylethylamine (1.25 mL), and sodium iodide (125.5 mg). The solution was heated to 95° C. for 2 hours and cooled. The reaction was diluted with toluene, washed with saturated Na$_2$CO$_3$, dried (Na$_2$SO$_4$), and concentrated. The product was purified by silica gel column (1: I EtOAc/hexanes) to provide 1.33 g (73%) of the title compound as a red-brown oil.
$^1$H NMR (300 MHz, CDCl$_3$) δ 6.8–7.2 (envelope, 4H), 3.45 (t, SH), 3.2 (t, 2H), 2.9 (t, 2H), 2.8 (t, 2H), 2.6 (m, 2H), 2.2 (s, 3H).

EXAMPLE 26B

N-(N'-benzyl-N'-methyl-2'-aminoethyl)-3-(2-methylphenyl)-1,2,5,6-tetrahydroisonicotine methyl ester A 25 mL round-bottom flask was charged with the product from Example 26A (203.0 mg, 0.6 mmol), N-benzylmethylamine (0.28 mL, 2.1 mmol), sodium iodide (20.5 mg, 10% by wt), and ethanol (1 mL). The reaction was heated to 80° C. for 12 hours. After cooling, the reaction was diluted with toluene, washed with saturated NaHCO$_3$, dried (MgSO$_4$), and concentrated. The product was diluted again with toluene and concentrated down. The product was purified by silica gel column (1% N11$_4$OH/EtOAc) to produce 122.3 mg (54%) of the title compound as an orange oil.
MS (ESI) m/z 379 (M+H)$^+$.

EXAMPLE 26C

N-2N'-benzyl-N'-methyl-2'-aminoethyl)-3-(2-methyphenyl)-1,2,5,6-tetrahydroisonicotine Following the procedure from Example 25B, the product from Example 26B (122.3 mg, 0.12 mmol) was converted to the title compound (95.4 mg, 78%).
$^1$H NMR (300 MHz, MeOD) δ 7.4 (m, 2H), 6.9–7.2 (envelope, 47 ), 4.15 (s, 1H), 3.9 (s, 1H), 3.1 (t, 2N), 3.0 (s, 3H), 2.85 (t, 2H), 2.75 (s, 3H), 2.6 (m, 2H), 2.45 (s, 2H), 2.2 (s, 3H).

EXAMPLE 26D

N-[4-(2'-benzyl-2'-methyl-2'-aminoethyl)-3-(2-methylp henyl)-1,2,5,6-tetrahydroisonicotinyl] methionine, methyl ester Following the procedure in Example 1G, the product from Example 26C (93 (.4 mg, 0.24 mmol) was converted to the title compound (60.7 mg, 50%).
MS (ESI(+)) m/z 510 (M+N)$^+$, (ESI(−)) 508 (M−H)$^-$.

EXAMPLE 26E

N-[4-(2',2'-di-butyl-2'-aminoethyl)-3-(2-methylphenyl)-1,2,5,6-tetrahydroisonicotinyl] methionine Following the procedure from Example 1J, the product from Example 26D (60.7 mg, 0.12 mmol) was converted to the title compound (50.5 mg, 86%).
$^1$H NMR (300 MHz, CDCl$_3$) δ 7.6 (br. s, 2H), 7.4 (br. 4n), 7.2 (br. I, 3N), 3.5–4.5 (envelope, 63), 3.05 (br. 3, 2H), 2.8 (br.s , 2H), 2.35 (br.s, 2H), 2.25 (br. s, 2H), 1.7–2.0 (envelope, 6H), 1.6 (br.m, 2H), 1.22 (s, 3H), 1.2 (s, 3H); MS (ESI(+)) m/z 496 (M+H)$^+$, (ESI(−)) 494 (M−H)$^−$; Anal. calc'd for C$_{28}$H$_{37}$N$_3$O$_3$S.5.0 H$_2$O: C, 57.41; H, 8.09; N, 7.17. Found: C, 57.40; H, 7.26; N, 6.18.

EXAMPLE 27

N-[4-((N'-(2-cyclohexyloxyethyl )-N'-butyl)-2'-aminoethyl)-3-(2-methylphenyl)-1,2,5,6-tetrahydroisonicotinyl]methionine, lithium salt

EXAMPLE 27A

N-Butyl-2-phenoxyactamide

A 100 mL 3-neck, round-bottom flask was charged with N-butylamine (8 mL, 80 mmol) and CH$_2$Cl$_2$ (20 mL) under N$_2$ purge. The reaction was cooled to −10° C. Phenoxylacetylchloride (2.8 mL, 20 mmol) was slowly added via syringe, and the reaction was stirred at −10° C. for 5 minutes and warmed to room temperature. After 2 hours, the solvent was removed under vacuum. The reaction was diluted with water and extracted with EtOAc (3×20 mL). The combined organic layers were washed with brine (20 mL), dried (Na$_2$SO$_4$), filtered, and concentrated under vacuum. The pale yellow oil crystallized upon standing to provide 4.32 g of the title compound as a pale yellow crystalline solid. MS (DCI/NH$_3$) m/z 225 (M+H)$^+$.

EXAMPLE 27B

N-Butyl-2-cyclohexyloxyacetamide

A solution of N-butylphenoxyatamide (Example 27A) in 5 mL of MeOH was treated with 5% rhodium on alumina and stirred under 4 atm of hydrogen gas for 24 hours. The mixture was filtered and concetrated to provide 1.823 g (88%) of the title compound as a pale yellow liquid.
MS (DCI/NH$_3$) m/z 214 (M+H)$^+$.

EXAMPLE 27C

N-2-cyclohexyloxyethylbutylamine

A 100 mL 3-neck, round-bottom flask with an addition funnel and reflux condenser was charged with the product from Example 27B (2.30 g, 10.78 mmol) and anhydrous THF (15 mL) under an N$_2$ atmosphere. The reaction was cooled to −10° C. 10M borane dimethylsulfide complex (3.4 mL, 32.35 mmol) was slowly added via the addition funnel and rinsed with an additional 5 mL of anhydrous THF. The reaction was stirred for 18 hours while warming to room temperature. TLC (1:1 EtOAc/hexanes) showed the reaction almost complete. Heat to reflux for 18 hours, monitoring by TLC. The reaction was cooled to room temperature and MeOH (6 mL) was slowly added with gas evolution resulting and stirred for 30 minutes. 12M HCl (3 mL) was slowly added with gas evolution. The reaction was again heated to reflux while monitoring the disappearance of the borate ester by TLC (1:1 EtOAc/hexane) and then cooled to room temperature. 1M NaOH (20 mL) was added and the reaction was extracted with Et$_2$O (3×20 mL). The pH of the aqueous layer was adjusted to 12 with 1M NaOH and then extracted with CH$_2$Cl$_2$ (3×20 mL). The combined organic layers were washed with brine, dried (Na$_2$SO$_4$), filtered and concentrated under vacuum to provide 1.35 mg (63%) of the title compound as a white solid.
MS (DCI/NH$_3$) m/z 200 (M+H)I.

EXAMPLE 27D

N-(N'-(2-cyclohexyloxyethyl)-N'-butyl-2'-aminoethyl)-3-(2-methylphenyl)-1,2,5,6-tetrahydroisonicotine, methyl ester Following the procedure from Example 26B, the product from Example 27C was converted to the title compound (187.7 mg, 55%).

MS (ESI(+)) m/z 457 (M+H)$^+$.

EXAMPLE 27E

N-(N'-(2-cyclohexyloxyethyl)-N'-butyl-2'-aminoethyl)-3-(2-methylphenyl)-1,2,5,6-tetrahydroisonicotine Following the procedure from Example 25B, the product from Example 27D (187.7 mg, 0.41 mmol) provided the title compound (137.8 mg, 76%) as a yellow oil. MS (ESI(+)) m/z 443(M+H)$^+$, (ESI(−)) 441 (M−H)$^−$.

EXAMPLE 27F

N-[4-((N'-(2-cyclohexyloxyethyl)-N'-butyl)-2'-aminoethyl)-3-(2-methylphenyl)-1,2,5,6-tetrahydroisonicotinyl]methionine, methyl ester Following the from procedure in Example 1 G, the product from Example 27E was converted to the title compound (114.1 mg 65%) as a yellow oil.
MS (ESI(+)) m/z 588 (M+H)$^+$, (ESI(−)) 586 (M−H)$^−$.

EXAMPLE 27G

N-[4-((N'-(2-cyclohexyloxyethyl)-N'-butyl)-2'-aminoethyl5−3-(2-methylphenyl)-1,2,5,6-tetrahydroisonicotinyl]methionine Following the procedure from Example 1J, the product from Example 27F was converted to the title compound (48.0 mg, 74%) as a white solid.
MS (ESI(+)) m/z 574 (M+H)$^+$, (ESI(−)) 572 (M−H)$^−$.

EXAMPLE 27H

N-[4-((N'-(2-cyclohexyloxyethyl)-N'-butyl)-2'-aminoethyl)-3-(2-methylphenyl)-1,2,5,6-tetrahydroisonicotinyl]methionine, lithium salt Following the procedure from Example 20D, the product from Example 27G (64.4 mg, 0.11 mmol) was converted to the title compound (48.0 mg, 74%).
$^1$H NMR (300 MHz, DMSO-d$_6$) δ 6.8–7.2 (envelope, 4H), 6.55 (br. s, IH), 3.0–3.6 (envelope 9H), 2.5–3.4 (envelope, 6H), 2.0–2.45 (envelope, 6H), 1.85 (s, 3H), 1.8 (s, 3H), 1.8 (s, 3H), 1.0–1.75 (envelope, 15H), 0.85 (t, 3H); MS (ESI(+)) m/z 574 (M+H)$^+$, (ESI(−)) 572 (M−H)$^−$. Anal. calc'd for C$_{32}$H$_{50}$LiN$_3$O$_4$S.3.5 H$_2$O: C, 59.79; H, 8.94; N, 6.54. Found: C, 59.82; H, 8.25; N, 6.23.

EXAMPLE 28

N-[4-(2(S)-(cyclohexyloxymethylpyrrolidinyl) ethyl)-3-(2-methylphenyl)-1,2,5,6-tetrahydroisonicotinyl]methionine, lithium salt

EXAMPLE 28A

N-t-Butoxycarbonyl-2(S)-phenoxymethylpyrrolidine

A solution of N-t-butoxycarbonyl-2-hydroxymethylpyrrolidine (0.80 g, 4.00 mmol), triphenylphosphine (2.10 g, 8.00 mmol), and phenol (1.13 g, 12.00 mmol) in 10 mL of 1,2-dichloromethane was cooled in an ice bath and treated with a solution of diethylazodicarboxylate (1.26 mL, 8.00 mmol) in 6 mL of toluene. The cooling bath was removed and the solution was stirred for 70 hours at ambient temperature. The mixture was diluted with ether and extracted with 4N aqueous sodium hydroxide, dried (Na$_2$SO$_4$), filtered and concentrated. The residue was purified by column chromatography on silica gel to provide (0.99 g, 89%) of the title compound.
MS (DCI/NH$_3$) m/z 278 (M+H)$^+$.

EXAMPLE 28B

N-t-Butoxycarbonyl-2(S)-cyclohexyloxymethylpyrrolidine

Following the procedure for Example 20A, the product from Example 28A (0.56 g, 2.00 mmol) was converted to the title compound (0.55 g, 96%).
MS (DCI/NH$_3$) m/z 284 (M+H)$^+$.

EXAMPLE 28C

2(S)-cyclohexyloxymethylpyrrolidine hydrochloride salt

Following the procedure for Example 1H, the product from Example 28B (0.54 g, 1.90 mmol) was converted to the title compound (0.41g, 99%).
MS (DCI/NH$_3$) m/z 184 (M+H)$^+$, 201 (M+NH$_4$)+.

EXAMPLE 28D

N-(2(S)-(cyclohexyloxymethylpyrrolidinyl)ethyl)-3-(2-methylphenyl)-1,2,5,6-tetrahydroisonicotine methyl ester Following the procedure from Example 26B, the product from Example 28C (173.0 mg, 0.79 mmol) was converted to the title compound (48.5 mg, 48%) as a red oil.
MS (ESI(+)) mn/z 441 (M+H)$^+$.

EXAMPLE 28E

N-(2(S)-(cyclohexyloxymethylpyrrolidinyl)ethyl)-3-(2-methylphenyl)-1,2,5,6-tetrahydroisonicotine Following the procedure Example 25B, the product from Example 28D (48.5 mg, 0.11 mmol) was converted to the title compound.
MS (ESI(+)) mn/z 427 (M+H)$^+$, (ESI(–)) 425 (M-H)$^-$.

EXAMPLE 28F

N-[4-(2(S)-(cyclohexyloxymethylpyrrolidinyl)ethyl)-3-(2-methylphenyl)-1,2,5,6-tetrahydroisonicotinyl]methionine, methyl ester Following the procedure from Example 1G, the product from Example 28E was converted to the title compound (19.8 mg, 37%) as an orange oil.
MS (ESI(+)) m/z 572 (M+H)$^+$, (ESI(-) 570 (M-H)$^-$.

EXAMPLE 28G

N-[4-(2(S)-(cyclohexyloxymethylpyrrolidinyl)ethyl)-3-(2-methylphenyl)-1,2,5,6-tetrahydroisonicotinyl]methionine lithium salt Following the procedure from Example 20D, the product from Example 28F was converted to the title compound (21.3 mg) as an orange/yellow solid.
$^1$H NMR (300 MHz, MeOD) δ 6.95–7.3 (envelope, 5H), 4.1 (br.s, 1H), 3.45 (dd, 2H), 2.8–3.3 (envelope, 8H), 2.7 (br.s, 3H), 2.0–2.6 (envelope, 8H), 1.95 (s, 3H), 1.1–1.9 (envelope, 15H), 0.95 (s, 1H); MS (ESI(+)) m/z 558 (M+H)$^+$, (ESI(–) 556 (M-H)$^-$; Anal. calc'd for C$_{31}$H$_{46}$LiN$_3$O$_4$S.3.8 H$_2$O: C, 58.90; H, 8.55; N, 6.65. Found: C, 58.87; H, 7.57; N, 6.28.

What is claimed is:

1. A compound of Formula I

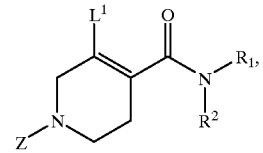

or a pharmaceutically acceptable salt thereof, where
L$^1$ is selected from
   (1) phenyl,
   (2) naphthyl,
   (3) dihydronaphthyl, and
   (4) tetrahydronaphthyl,
      where (1)–(4) can be optionally substituted with 1 or 2 substituents independently selected from
      (a) alkyl,
      (b) halogen,
      (c) perfluoroalkyl, and
      (d) —OR$^3$ where R$^3$ is selected from
         (a) hydrogen and
         (b) alkyl;
R$^1$ is hydrogen;
R$^2$ is selected from
   (1) alkyl where the alkyl can be optionally substituted with 1, 2, or 3 substituents independently selected from
      (a) —CO$_2$R$^4$ where R$^4$ is selected from
         (i) hydrogen,
         (ii) alkyl, and
         (iii) a carboxy-protecting group
         and
      (b) —S(O)$_r$R$^7$,
         where R$^7$ is selected from
         (i) hydrogen,
         (ii) alkyl, and
         (iii) aryl,
and
Z is
   —C(O)R$^{12}$ where R$^{12}$ is
      where R$^{16}$ is alkyl, where the alkyl is substituted with 1, 2, or 3 cycloalkyl substituents.

2. A compound according to claim 1 where L$^1$ is phenyl and R$^2$ is alkyl substituted with one —CO$_2$R$^4$ and one —S(O)$_r$R$^7$ substituent.

3. A compound according to claim 2 where R$^4$ is hydrogen.

4. A compound according to claim 3 where R$^7$ is methyl.

5. A compound according to claim 4 which is
   N-4-[1-(3-Cyclohexylpropyloxycarbonyl)-3-(2-methylphenyl)-1,2,5,6-tetrahydroisonicotinyl] methionine.

6. A method of inhibiting protein isoprenyl transferases in a mammal in need of such treatment comprising administering to the mammal a therapeutically effective amount of a compound of claim 1.

7. A composition for inhibiting protein isoprenyl transferases comprising a pharmaceutical carrier and a therapeutically effective amount of a compound of claim 1.

* * * * *